(12) United States Patent
Khatibi et al.

(10) Patent No.: US 12,245,779 B2
(45) Date of Patent: Mar. 11, 2025

(54) PATIENT-SPECIFIC INSTRUMENTATION AND METHODS FOR ANKLE ARTHROPLASTY

(71) Applicant: Orthosoft ULC, Montreal (CA)

(72) Inventors: Bahareh Khatibi, Montreal (CA); Jeremie Menard, Montreal (CA); Trong-Tin Nguyen, Laval (CA); Jean-Francois Girouard, Terrasse-Vaudreuil (CA); Antony Bou-Francis, Verdun (CA); Quentin Derouault, Montreal (CA); Nicholas Boudreau, Repentigny (CA); Sandra Snyder, Plymouth, IN (US)

(73) Assignee: Orthosoft ULC

( * ) Notice: Subject to any disclaimer, the term of this patent is extended or adjusted under 35 U.S.C. 154(b) by 0 days.

(21) Appl. No.: 18/500,633

(22) Filed: Nov. 2, 2023

(65) Prior Publication Data
US 2024/0058021 A1 Feb. 22, 2024

Related U.S. Application Data

(63) Continuation of application No. 17/072,645, filed on Oct. 16, 2020, now Pat. No. 11,849,961.
(Continued)

(51) Int. Cl.
*A61B 17/17* (2006.01)
*A61B 17/15* (2006.01)
(Continued)

(52) U.S. Cl.
CPC .......... *A61B 17/1775* (2016.11); *A61B 17/15* (2013.01); *A61F 2/4606* (2013.01); *A61B 2034/108* (2016.02); *A61F 2002/4207* (2013.01)

(58) Field of Classification Search
CPC ............ A61B 17/1775; A61B 17/1739; A61B 17/1757; A61B 17/151; A61B 17/157;
(Continued)

(56) References Cited

U.S. PATENT DOCUMENTS 7,172,596 B2 2/2007 Coon et al.
7,534,263 B2 5/2009 Burdulis, Jr. et al.
(Continued)

FOREIGN PATENT DOCUMENTS

CN 102405024 4/2012
CN 104661619 5/2015
(Continued)

OTHER PUBLICATIONS

US 8,849,621 B2, 09/2014, Fitz et al. (withdrawn)
(Continued)

*Primary Examiner* — Anu Ramana
(74) *Attorney, Agent, or Firm* — SCHWEGMAN LUNDBERG & WOESSNER, P.A.

(57) ABSTRACT

Patient-specific guide systems and methods for performing bone resections for ankle arthroplasties comprises a bone guide body and a bone resection block. The bone guide body comprises a patient-specific surface for engaging a surface of a talus or a tibia, and a first pin hole and a first socket in the bone guide body. The bone resection block is removably insertable into the first socket, receives a first pin that can be inserted in the first pin hole, and includes a resection guide surface. The system further comprises a floating bone trial that attaches to the bone resection block via a floating bone guide. The floating bone trail receives a chamfer spacer and guide for further resecting the bone. The system further comprises a stylus for engagement with the resection guide
(Continued)

surface to confirm resection depth. The bone guide body includes alignment pin and resection block snap lock features.

20 Claims, 32 Drawing Sheets

Related U.S. Application Data

(60) Provisional application No. 62/923,301, filed on Oct. 18, 2019.

(51) Int. Cl.
*A61F 2/46* (2006.01)
*A61B 34/10* (2016.01)
*A61F 2/42* (2006.01)

(58) Field of Classification Search
CPC .. A61F 2/42; A61F 2/4202; A61F 2002/4207; A61F 2/4606
See application file for complete search history.

(56) References Cited

U.S. PATENT DOCUMENTS

| | | | |
|---|---|---|---|
| 7,569,067 B2 * | 8/2009 | Keller | A61F 2/4611 |
| | | | 606/208 |
| 7,618,451 B2 | 11/2009 | Berez et al. | |
| 7,963,971 B2 * | 6/2011 | Keller | A61B 17/025 |
| | | | 606/99 |
| 7,981,158 B2 | 7/2011 | Fitz et al. | |
| 8,062,302 B2 | 11/2011 | Lang et al. | |
| 8,083,745 B2 | 12/2011 | Lang et al. | |
| 8,105,330 B2 | 1/2012 | Fitz et al. | |
| 8,337,503 B2 * | 12/2012 | Lian | A61B 17/15 |
| | | | 606/87 |
| 8,366,771 B2 | 2/2013 | Burdulis, Jr. et al. | |
| 8,460,304 B2 | 6/2013 | Fitz et al. | |
| 8,475,463 B2 * | 7/2013 | Lian | A61B 17/15 |
| | | | 606/87 |
| 8,551,169 B2 | 10/2013 | Fitz et al. | |
| 8,585,708 B2 | 11/2013 | Fitz et al. | |
| 8,617,172 B2 | 12/2013 | Fitz et al. | |
| 8,657,827 B2 | 2/2014 | Fitz et al. | |
| 8,808,303 B2 * | 8/2014 | Stemniski | A61F 2/4202 |
| | | | 606/96 |
| 8,951,259 B2 | 2/2015 | Fitz et al. | |
| 8,968,320 B2 | 3/2015 | Park et al. | |
| 8,998,915 B2 | 4/2015 | Fitz et al. | |
| 9,017,414 B2 * | 4/2015 | Grecco | A61F 2/4684 |
| | | | 623/20.14 |
| 9,023,050 B2 | 5/2015 | Lang et al. | |
| 9,066,728 B2 | 6/2015 | Burdulis, Jr. et al. | |
| 9,072,531 B2 | 7/2015 | Fitz et al. | |
| 9,107,680 B2 | 8/2015 | Fitz et al. | |
| 9,125,672 B2 | 9/2015 | Fitz et al. | |
| 9,125,673 B2 | 9/2015 | Fitz et al. | |
| 9,125,674 B2 | 9/2015 | White et al. | |
| 9,186,154 B2 | 11/2015 | Li | |
| 9,186,161 B2 | 11/2015 | Lang et al. | |
| 9,216,025 B2 | 12/2015 | Fitz et al. | |
| 9,220,517 B2 | 12/2015 | Lang et al. | |
| 9,220,518 B2 | 12/2015 | Neal et al. | |
| 9,295,482 B2 | 3/2016 | Fitz et al. | |
| 9,295,554 B2 * | 3/2016 | Gillard | A61F 2/4202 |
| 9,326,780 B2 | 5/2016 | Wong et al. | |
| 9,358,018 B2 | 6/2016 | Fitz et al. | |
| 9,414,847 B2 | 8/2016 | Kurtz | |
| 9,492,178 B2 | 11/2016 | Neal et al. | |
| 9,532,845 B1 | 1/2017 | Dossett et al. | |
| 9,675,365 B2 | 6/2017 | Lancianese et al. | |
| 9,730,714 B2 | 8/2017 | Lian | |
| 9,795,399 B2 | 10/2017 | Metzger et al. | |
| 9,861,446 B2 | 1/2018 | Lang | |
| 9,907,561 B2 | 3/2018 | Luna et al. | |
| 9,918,724 B2 | 3/2018 | Luna et al. | |
| 9,980,780 B2 | 5/2018 | Lang | |
| 9,993,255 B2 | 6/2018 | Mcginley et al. | |
| 10,136,904 B2 * | 11/2018 | McGinley | A61B 90/39 |
| 10,159,530 B2 | 12/2018 | Lang | |
| 10,182,832 B1 * | 1/2019 | Saltzman | A61B 17/1775 |
| 10,278,777 B1 | 5/2019 | Lang | |
| 10,292,768 B2 | 5/2019 | Lang | |
| 10,314,597 B2 * | 6/2019 | Saltzman | A61B 17/1682 |
| 10,327,785 B2 | 6/2019 | Bake et al. | |
| 10,426,494 B2 * | 10/2019 | Saltzman | A61B 17/1775 |
| 11,000,296 B2 * | 5/2021 | Loring | A61F 2/4606 |
| 11,090,069 B2 | 8/2021 | Park | |
| 11,399,949 B2 * | 8/2022 | Dogué | A61F 2/4684 |
| 11,439,469 B2 * | 9/2022 | Poltaretskyi | G16H 80/00 |
| 11,464,522 B2 * | 10/2022 | Dalton | A61B 17/1604 |
| 11,517,444 B2 * | 12/2022 | McDonough | A61F 2/4465 |
| 11,529,152 B2 * | 12/2022 | Free | A61B 17/1775 |
| 11,571,263 B2 * | 2/2023 | Moore | A61B 5/1114 |
| 11,690,636 B2 * | 7/2023 | Free | A61B 17/1682 |
| | | | 606/87 |
| 11,723,676 B2 * | 8/2023 | Loring | A61F 2/4606 |
| | | | 606/96 |
| 11,819,224 B2 * | 11/2023 | Allard | A61B 17/15 |
| 11,849,961 B2 | 12/2023 | Khatibi et al. | |
| 11,857,207 B2 * | 1/2024 | Free | A61G 13/1245 |
| 2002/0029045 A1 | 3/2002 | Bonutti | |
| 2004/0236424 A1 | 11/2004 | Berez et al. | |
| 2005/0171545 A1 | 8/2005 | Walsh et al. | |
| 2005/0234461 A1 | 10/2005 | Burdulis, Jr. et al. | |
| 2005/0273115 A1 | 12/2005 | Coon et al. | |
| 2008/0243127 A1 | 10/2008 | Lang et al. | |
| 2008/0275452 A1 | 11/2008 | Lang et al. | |
| 2009/0088763 A1 | 4/2009 | Aram et al. | |
| 2009/0222014 A1 | 9/2009 | Bojarski et al. | |
| 2010/0087824 A1 | 4/2010 | Collazo | |
| 2010/0217338 A1 * | 8/2010 | Carroll | A61B 17/151 |
| | | | 606/86 R |
| 2010/0262150 A1 | 10/2010 | Lian | |
| 2011/0066193 A1 | 3/2011 | Lang et al. | |
| 2011/0092804 A1 | 4/2011 | Schoenefeld et al. | |
| 2011/0218542 A1 | 9/2011 | Lian | |
| 2012/0022884 A1 | 1/2012 | Chillemi | |
| 2012/0130434 A1 | 5/2012 | Stemniski | |
| 2012/0239045 A1 | 9/2012 | Li et al. | |
| 2012/0289966 A1 | 11/2012 | Fitz et al. | |
| 2012/0310400 A1 | 12/2012 | Park et al. | |
| 2013/0030419 A1 | 1/2013 | Fitz et al. | |
| 2013/0085499 A1 | 4/2013 | Lian | |
| 2013/0123792 A1 | 5/2013 | Fitz et al. | |
| 2013/0184713 A1 | 7/2013 | Bojarski et al. | |
| 2014/0031827 A1 | 1/2014 | Lancianese et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0114320 A1 | 4/2014 | Kurtz | |
| 2014/0236159 A1 | 8/2014 | Haider et al. | |
| 2014/0324053 A1 | 10/2014 | Stemniski et al. | |
| 2014/0324058 A1 | 10/2014 | Metzger et al. | |
| 2014/0336658 A1 | 11/2014 | Luna et al. | |
| 2015/0039037 A1 | 2/2015 | Donner et al. | |
| 2015/0057665 A1 | 2/2015 | Neal et al. | |
| 2015/0157340 A1 | 6/2015 | Mcginley et al. | |
| 2015/0257899 A1 | 9/2015 | Luna et al. | |
| 2016/0089153 A1 | 3/2016 | Couture et al. | |
| 2016/0128701 A1 | 5/2016 | Neal et al. | |
| 2016/0213491 A1 | 7/2016 | Schoenefeld et al. | |
| 2016/0256293 A1 | 9/2016 | Mauldin et al. | |
| 2016/0361071 A1 | 12/2016 | Mahfouz | |
| 2016/0367269 A9 | 12/2016 | Mcginley et al. | |
| 2017/0100140 A1 | 4/2017 | Stemniski et al. | |
| 2017/0112509 A9 | 4/2017 | Lancianese et al. | |
| 2017/0150963 A1 | 6/2017 | Coleman | |
| 2017/0258526 A1 | 9/2017 | Lang | |
| 2017/0281999 A1 | 10/2017 | Lilley | |

(56) References Cited

U.S. PATENT DOCUMENTS

| | | |
|---|---|---|
| 2017/0296208 A1 | 10/2017 | Lian |
| 2017/0325826 A1 | 11/2017 | Bake et al. |
| 2017/0367766 A1 | 12/2017 | Mahfouz |
| 2018/0085133 A1 | 3/2018 | Lavallee et al. |
| 2018/0116728 A1 | 5/2018 | Lang |
| 2018/0125584 A1 | 5/2018 | Lang |
| 2018/0146970 A1 | 5/2018 | Luna et al. |
| 2018/0153558 A1 | 6/2018 | Bake et al. |
| 2018/0177511 A1 | 6/2018 | Luna et al. |
| 2018/0193035 A1 | 7/2018 | Couture et al. |
| 2018/0235641 A1 | 8/2018 | Mcauliffe et al. |
| 2018/0263639 A1 | 9/2018 | Mcginley et al. |
| 2018/0263704 A1 | 9/2018 | Lang |
| 2018/0289380 A1 | 10/2018 | Mauldin et al. |
| 2018/0360477 A1 | 12/2018 | Singh et al. |
| 2019/0038298 A1 | 2/2019 | Bojarski et al. |
| 2019/0053840 A1 | 2/2019 | Mcginley et al. |
| 2019/0110842 A1 | 4/2019 | Lang |
| 2019/0167274 A1 | 6/2019 | Dhillon |
| 2019/0167352 A1 | 6/2019 | Mahfouz |
| 2021/0113222 A1 | 4/2021 | Khatibi et al. |

FOREIGN PATENT DOCUMENTS

| | | |
|---|---|---|
| CN | 106456190 | 2/2017 |
| CN | 107789097 | 3/2018 |
| CN | 114585314 A | 6/2022 |
| WO | WO-2012088036 A1 | 6/2012 |
| WO | WO-2012125319 A1 | 9/2012 |
| WO | WO-2019091537 A1 | 5/2019 |
| WO | WO-2021072544 A1 | 4/2021 |

OTHER PUBLICATIONS

"U.S. Appl. No. 17/072,645, Non Final Office Action mailed Apr. 25, 2023", 10 pgs.

"U.S. Appl. No. 17/072,645, Notice of Allowance mailed Aug. 2, 2023", 8 pgs.

"U.S. Appl. No. 17/072,645, Preliminary Amendment filed Jun. 24, 2022", 7 pgs.

"U.S. Appl. No. 17/072,645, Response filed Jan. 26, 2023 to Restriction Requirement mailed Dec. 9, 2022", 8 pgs.

"U.S. Appl. No. 17/072,645, Response filed Jul. 17, 2023 to Non Final Office Action mailed Apr. 25, 2023", 16 pgs.

"U.S. Appl. No. 17/072,645, Restriction Requirement mailed Dec. 9, 2022", 5 pgs.

"Canadian Application Serial No. 3,157,160, Examiners Rule 86(2) Report mailed Sep. 20, 2023", 3 pgs.

"European Application Serial No. 20877549.4, Extended European Search Report mailed Sep. 28, 2023", 5 pgs.

"European Application Serial No. 20877549.4, Response to Communication pursuant to Rules 161(2) and 162 EPC filed Dec. 7, 2022", 20 pgs.

"International Application Serial No. PCT/CA2020/051386, International Preliminary Report on Patentability mailed Apr. 19, 2022", 6 pgs.

"International Application Serial No. PCT/CA2020/051386, International Search Report mailed Jan. 12, 2021", 5 pgs.

"International Application Serial No. PCT/CA2020/051386, Written Opinion mailed Jan. 12, 2021", 5 pgs.

"U.S. Appl. No. 17/072,645, Corrected Notice of Allowability mailed Nov. 16, 2023", 3 pgs.

"Canadian Application Serial No. 3,157,160, Response Filed Jan. 17, 2024 toExaminers Rule 86(2) Report mailed Sep. 20, 2023", 34 pgs.

"Chinese Application Serial No. 202080072549.5, Office Action mailed Jul. 3, 2024", w English translation, 14 pgs.

"European Application Serial No. 20877549.4, Communication Pursuant to Article 94(3) EPC mailed Sep. 18, 2024", 4 pgs.

"European Application Serial No. 20877549.4, Response filed Apr. 29, 2 to Extended European Search Report mailed Sep. 28, 2023", 3 pgs.

"European Application Serial No. 20877549.4, Response filed Jan. 15, 2024 to Communication Pursuant to Article 94(3) EPC mailed Sep. 18, 2024", 6 pgs.

"Chinese Application Serial No. 202080072549.5, Office Action mailed Jan. 11, 2025", W English Translation, 16 pgs.

\* cited by examiner

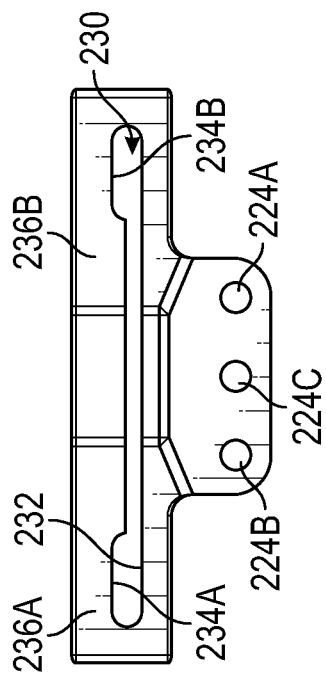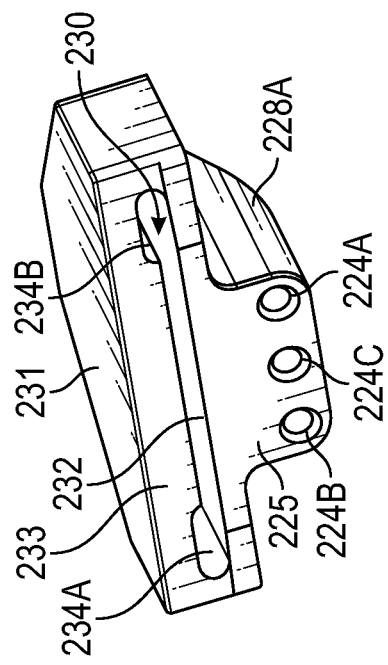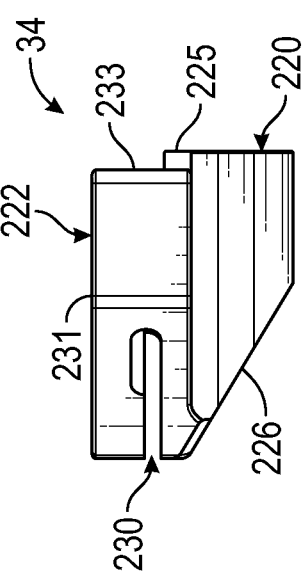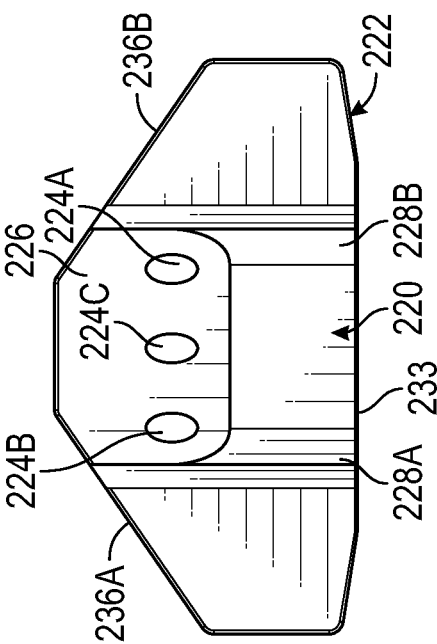

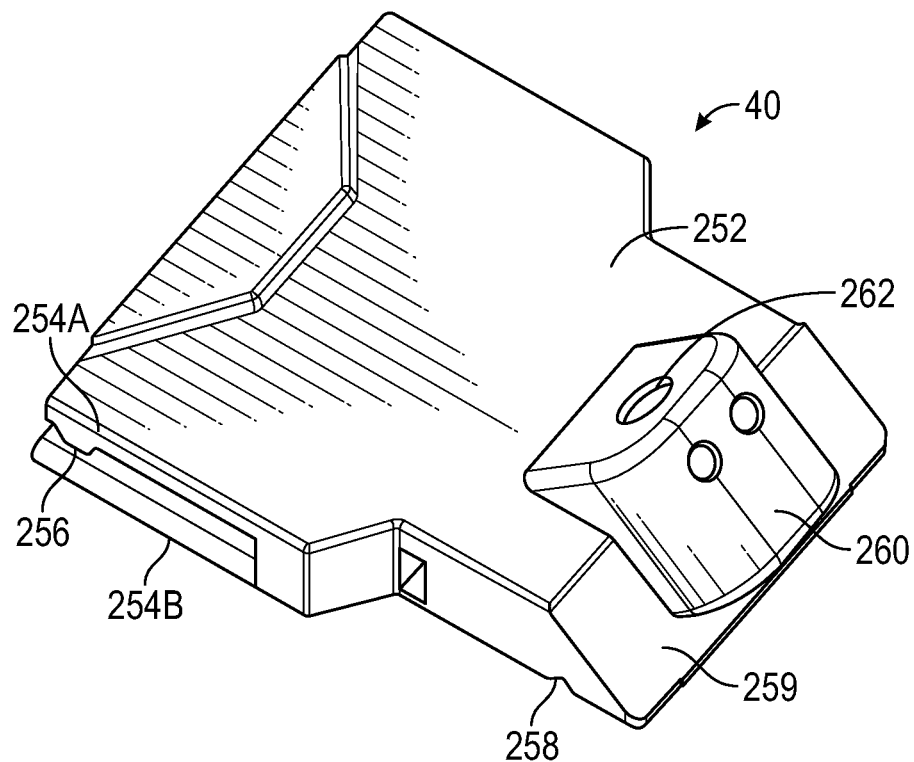
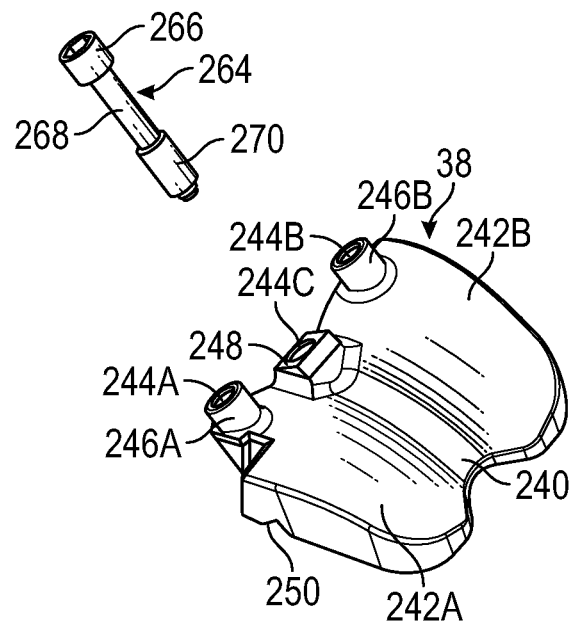
FIG. 10D

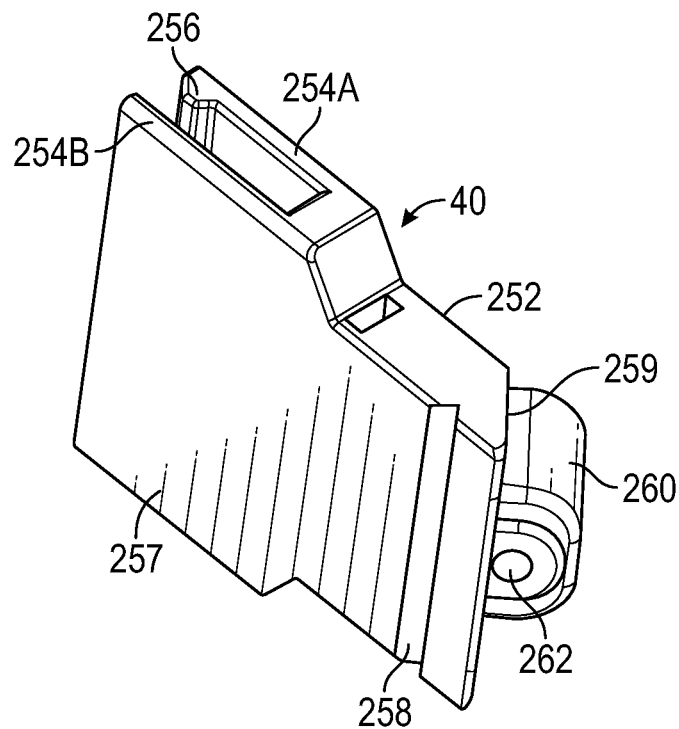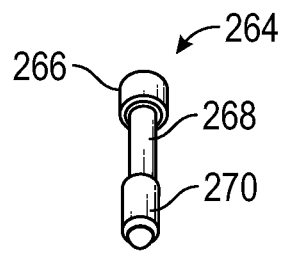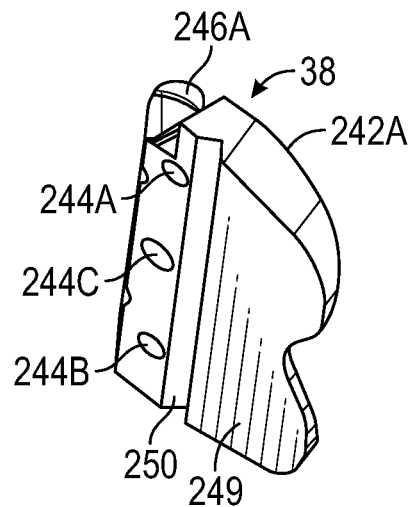
FIG. 10E

PATIENT-SPECIFIC INSTRUMENTATION AND METHODS FOR ANKLE ARTHROPLASTY

CLAIM OF PRIORITY

This application is a continuation of U.S. patent application Ser. No. 17/072,645, filed on Oct. 16, 2020, which claims the benefit of U.S. Provisional Patent Application Ser. No. 62/923,301, filed on Oct. 18, 2019, the benefit of priority of which is claimed hereby, and which is incorporated by reference herein in its entirety.

BACKGROUND

The present disclosure is directed to devices and methods for use in performing ankle arthroplasty, such as total ankle replacement procedures.

Patient-specific instruments have been successfully deployed for many surgical procedures. By creating three-dimensional (3D) models of anatomy of a patient from medical images, surgeries can be customized using virtual 3D surgical planning for specific patients. The virtual 3D surgical planning can be used to produce patient-specific cutting guides and instruments, which fit over the anatomy of the specific patient in a unique way to allow for precise replication of the planned surgery as compared to arthroplasty with conventional instrumentation.

U.S. Pat. No. 8,337,503 to Lian and Pub. No. US 2016/0361071 to Mahfouz describe cutting guides and instruments for use in total ankle replacement surgery.

OVERVIEW

The present inventors have recognized, among other things, that a problem to be solved can include designing patient-specific surgical guides that can be used to perform different sized cuts. For example, cutting guide surfaces or slots used to resect bone can be sized to produce standard cuts, wide cuts or narrow cuts, depending on the size of an anatomic feature of a specific patient. Sometimes, the size of the desired resection cannot be confirmed until access to the bone is achieved intraoperatively. If the size of the anatomic feature differs from the surgical plan, such that a different sized cutting surface is desired, it can sometimes become necessary to revert to use of standard, non-patient-specific instrumentation that can result in more complex, time-consuming procedures and potentially less accurate resections. Alternatively, production of multiple, patient-specific devices for contingencies can be expensive and wasteful.

The present inventors have additionally recognized that a problem to be solved can include damaging of patient-specific devices during resection procedures. Patient-specific devices can often be fabricated from materials that can be easily shaped to the contours of the anatomy of the specific patient. However, such materials can be softer than bone and can, therefore, be inadvertently cut during the resection procedure. This can result in revision of the surgical plan or potentially ill-fitting implants.

The present subject matter can help provide a solution to these and other problems, such as by providing modular patient-specific instrumentation wherein only the bone-engaging portion is patient-specific, while other portions can be generic to the surgical system being implanted. For example, cutting guide components having cutting surfaces or slots can be produced in different sizes, but with a common interface for engaging a socket of a bone-engaging, patient-specific component. As such, the cutting guide components can be mass produced and reusable, while only a single, disposable patient-specific component for each patient can be produced. Furthermore, the cutting guide components can be fabricated from a hard material that can withstand engagement from a cutting tool, thereby shielding both the bone and the patient-specific portion.

In an example, a patient-specific guide system for performing a talus resection for a total ankle arthroplasty can comprise a talus guide body, a talus resection block, a floating talar guide and a floating talar trial. The talus guide body can comprise a first patient-specific surface for engaging at least a portion of an anterior surface of a talus, a first pin hole extending through the talus guide body, and a first socket extending into the talus guide body. The talus resection block can comprise a coupling block removably insertable into the first socket, a second pin hole configured to align with the first pin hole, and a guide block including a resection guide surface. The floating talar guide can be couplable to the talus resection block and configured to extend beyond the first patient-specific surface. The floating talar trial can be couplable to the floating talar guide, the floating talar trial including a bearing surface and being configured to extend co-planar with the resection guide surface.

In another example, a method for performing a total-ankle arthroplasty can comprise resecting a portion of a tibia bone, attaching a patient-specific talus guide body to a superior portion of a talus bone, attaching a size-specific talus cutting block to the patient-specific talus guide body, resecting a superior portion of the talus, attaching a talus trialing component to the talus cutting block, confirming position of the talus trialing component, coupling the talus trialing component to the talus bone, removing the talus cutting block and the patient-specific talus guide body from the talus bone, chamfering an anterior portion of the talus bone using a chamfer guide attached to the talus trialing component, and attaching prosthetic ankle components to the resected tibia and talus bones.

In an additional example, a patient-specific guide for performing a bone resection for a total ankle arthroplasty can comprise a bone guide body and a bone resection block. The bone guide body can comprise a patient-specific surface for engaging a surface of a talus or a tibia, a first pin hole extending through the bone guide body, and a first socket extending through the bone guide body. The bone resection block can be removably insertable into the first socket and configured to receive a first pin that can be inserted in the first pin hole. The bone resection block can also include a resection guide surface.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIGS. 9A, 9B, 9C and 9D are side, front, bottom and perspective views of a talus resection block for use with the patient-specific talus guide body of FIGS. 8A-8G.

FIG. 10D is an exploded perspective top view of the floating talar trial and floating talar guide assembly of FIGS. 10A-10C.

FIG. 10E is an exploded perspective bottom view of the floating talar trial and floating talar guide assembly of FIGS. 10A-10C.

Figure 1:
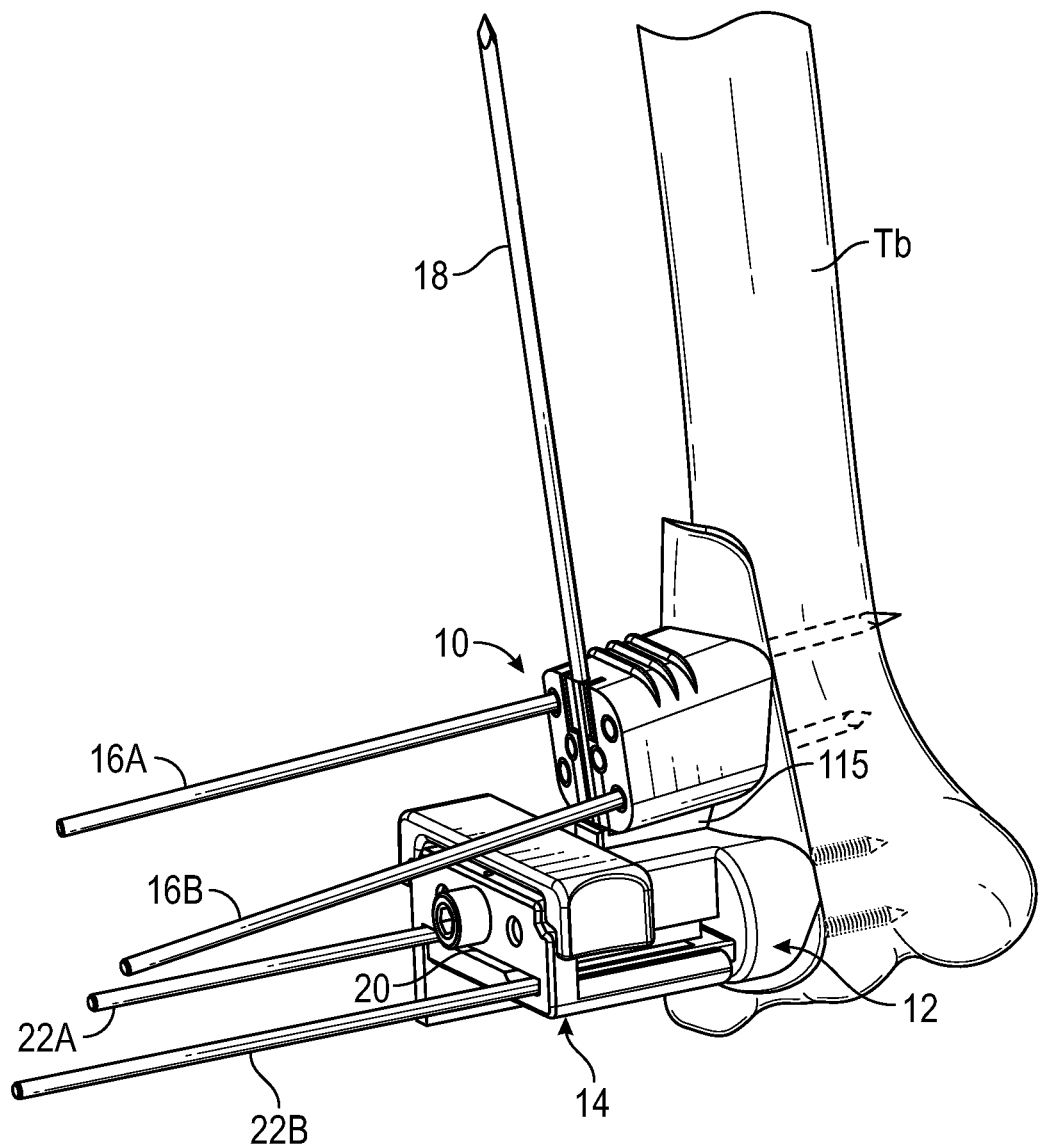
FIG. 1 is a perspective view of a tibia cut guide for a total ankle replacement procedure according to examples of the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

It should be understood that the following detailed description of embodiments of the present invention are exemplary in nature and are not intended to constitute limitations upon the present invention. It is also to be understood that variations of the exemplary embodiments contemplated by one of ordinary skill in the art shall concurrently fall within the scope and spirit of the invention.

FIG. 1 is a perspective view of tibia cut guide 10 for a total ankle replacement procedure according to an example of the present disclosure. Tibia cut guide can comprise patient-specific tibia guide body 12 and tibia resection block 14. Tibia guide body 12 can be secured to tibia Tb using pins 16A and 16B. Alignment of tibia resection block 14 with tibia Tb can be checked with alignment pin 18. Tibia resection block 14 can comprise cutting guide surface 20.

Pins 22A and 22B can be positioned against cutting guide surface 20 to shield tibia guide body 12 from contact of a cutting tool and to protect anatomy. As discussed in greater detail below, tibia cut guide 10 can comprise a modular component such that tibia guide body 12 can be patient-specific while tibia resection block 14 can be standardized and can be configured in different sizes, e.g, be size-specific, to produce different sized cuts.

Tibia cut guide 10 can be used in conjunction with talus cut guide 30 (FIG. 2) to perform a total ankle arthroplasty.

Figure 2:
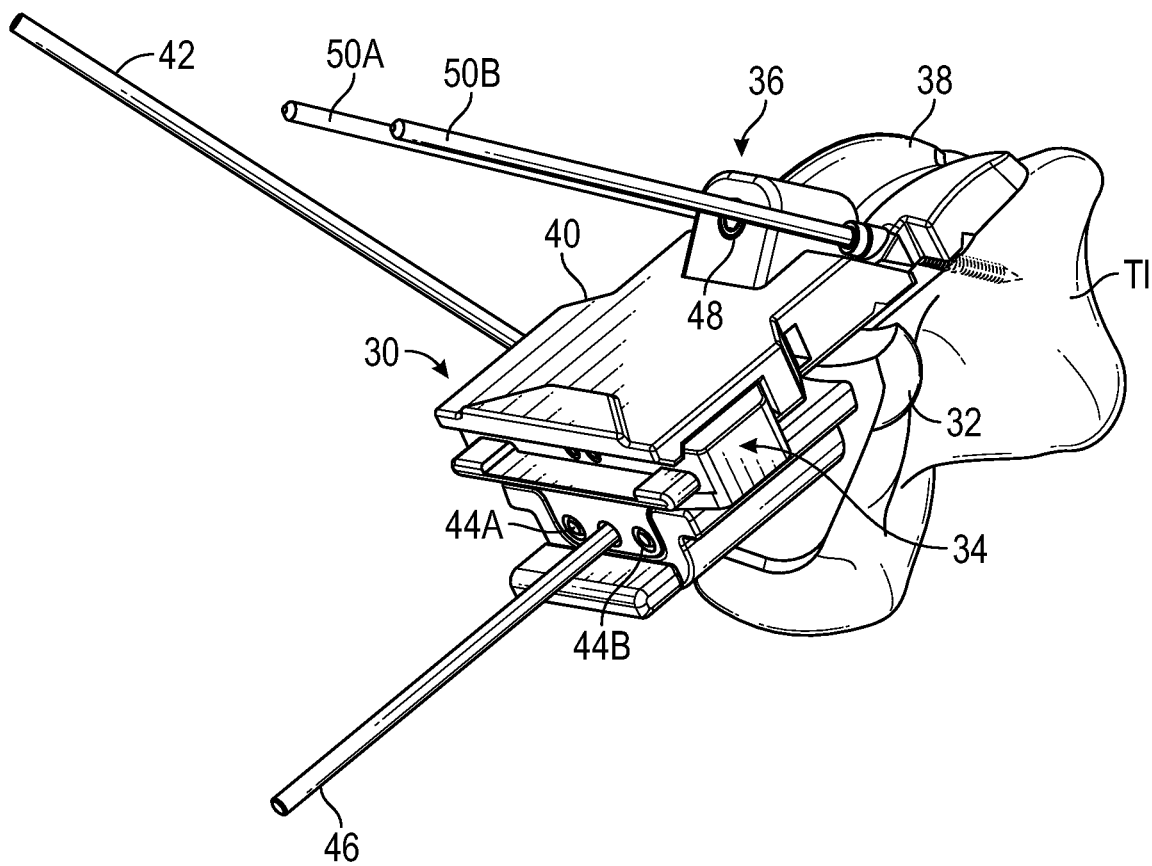
FIG. 2 is a perspective view of a talus cut guide for a total ankle replacement procedure according to examples of the present disclosure.

FIG. 2 is a perspective view of talus cut guide 30 for a total ankle replacement procedure according to an example of the present disclosure.

Talus cut guide 30 can comprise patient-specific talus guide body 32, talus resection block 34 and talar trial device 36. Talar trial device 36 can comprise floating talar trial 38 and floating talar guide 40. Talus guide body 32 can be secured to talus Tl using anchor pin 42. Furthermore, talus resection block 34 can be secured to talus guide body 32 via pins 44A and 44B. Alignment pin 46 can be inserted through talus resection block 34 and talus guide body 32 to facilitate coupling and uncoupling of talus resection block 34 from talus guide body. Floating talar trial 38 can be attached to floating talar guide 40 via fastener 48. Floating talar trial 38 can be secured to talus Tl via pins 50A and 50B. As discussed in greater detail below, talus cut guide 30 can comprise a modular component such that talus guide body 32 can be patient-specific while talus resection block 34 can be standardized and can be configured in different sizes, e.g, be size-specific, to produce different sized cuts.

Tibia cut guide 10 and talus cut guide 30 can be used to resect tibia Tb and talus Tl, respectively, to prepare an ankle joint for prosthetic ankle device 60 of FIG. 3.

In the following discussion, the terms "patient-specific," "custom-made" or "customized" are defined to apply to components, including tools such as alignment or drilling guides, implants, portions or combinations thereof, which include certain geometric features, including surfaces, curves, or other lines, and which are made to closely or nestingly conform and mate substantially as mirror-images or negatives or complementary surfaces of corresponding geometric features or anatomic landmarks of a patient's anatomy obtained or gathered during a pre-operative planning stage based on 3-D computer images of the corresponding anatomy reconstructed from image scans of the patient by computer imaging methods. Further, patient-specific guiding features, such as, guiding bores or other holes or openings that are included in patient-specific guides are defined as features that are made to have positions, orientations, dimensions, and axes specific to the particular patient's anatomy including various anatomic or reverse alignment axes based on the computer-assisted pre-operative plan associated with the patient.

Figure 3A:
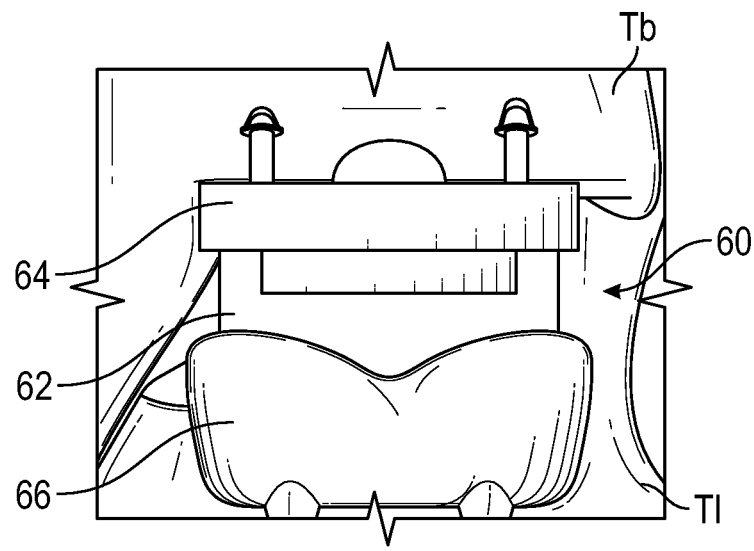
FIG. 3A is a schematic view of a prosthetic ankle component implanted in tibia and talus bones.
Figure 3B:
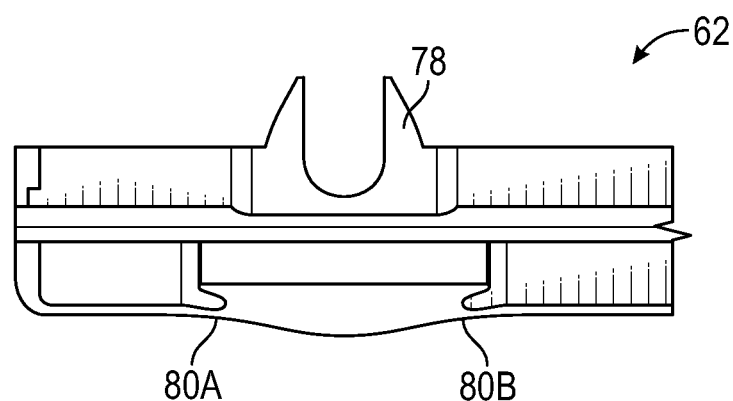
FIGS. 3B, 3C and 3D are perspective views of a tibial bearing component, a tibial tray component, and a talar bearing component, respectively, of the prosthetic ankle component of FIG. 3A, for use as a total ankle arthroplasty prosthetic that can be implanted with the tibia cut guide and talus cut guide of FIGS. 1 and 2.
Figure 3C:
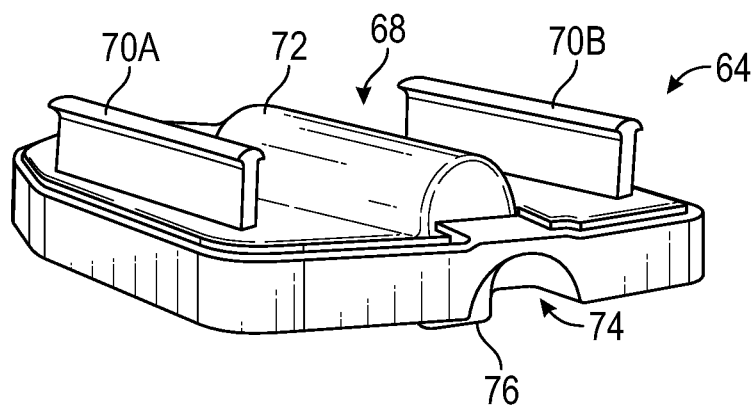
Figure 3D:
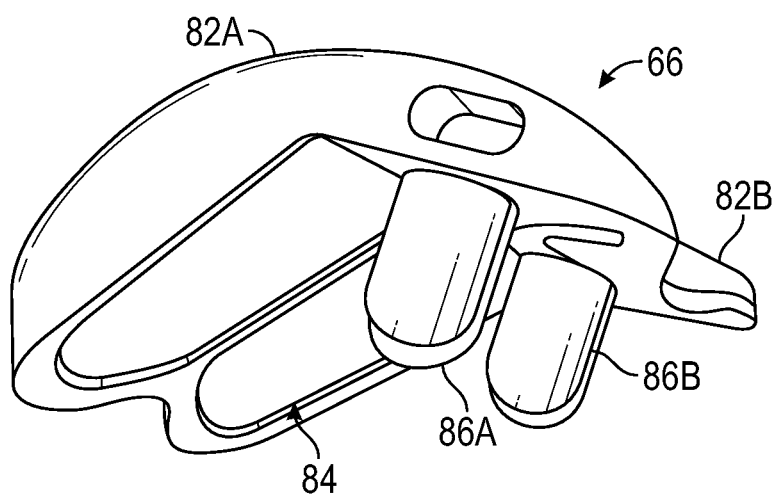

FIG. 3A is perspective view of prosthetic ankle device 60 for use as a total ankle arthroplasty prosthetic that can be implanted with tibia cut guide 10 and talus cut guide 30 of FIGS. 1 and 2, respectively. FIGS. 3B, 3C and 3D are perspective views of tibial bearing component 62, tibial tray component 64, and talar bearing component 66, respectively, that together form prosthetic ankle device 60.

As shown in FIG. 3A, tibial tray component 64 can be attached to tibia Tb and talar bearing component 66 can be attached to talus Tl. Tibial bearing component 62 can be attached to tibial tray component 64 for engagement with talar bearing component 66.

With reference to FIG. 3C, tibial tray component 64 can comprise bone-facing side 68 that can include fixation devices 70A and 70B and protrusion 72. Bone-facing side 68 can include a layer of porous material and protrusion 72 can be formed of porous material to facilitate bone ingrowth. Tibial tray component 64 can also comprise attachment side 74 that can include attachment feature 76 for engaging tibial bearing component 62.

With reference to FIG. 3B, tibial bearing component 62 can comprise attachment feature 78 for engaging attachment feature 76. In examples, attachment features 76 and 78 can comprise a snap-fit interface or any other suitable device for attaching tibial bearing component 62 and tibial tray component 64 into a locked configuration such that movement therebetween is inhibited. Tibial bearing component 62 can additionally include bearing surfaces 80A and 80B. Bearing surfaces 80A and 80B can be shaped to provide a smooth interface against which talar bearing component 66 can side against. Tibial bearing component 62 can be configured in different sizes to accommodate different sized ankle joints for different patients.

With reference to FIG. 3D, talar bearing component 66 can comprise bearing surfaces 82A and 82B that can engage bearing surfaces 80A and 80B, respectively. In examples, bearing surfaces 80A and 80B can be shaped as condyles, or smooth humps, to engage concavities formed by bearing surfaces 80A and 80B. Talar bearing component 66 can comprise bone-facing side 84 that can include fixation features 86A and 86B. Talar bearing component 66 can be configured in different sizes to accommodate different sized ankle joints for different patients.

Figure 4:
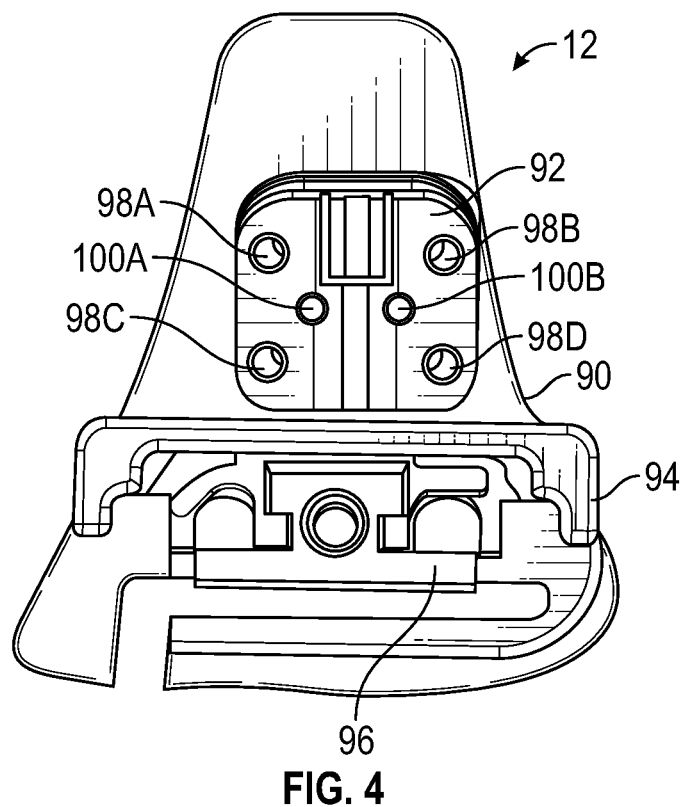
FIG. 4 is a front view of a patient-specific tibia guide body of the tibia cut guide of FIG. 1.

FIG. 4 is a front view of patient-specific tibia guide body 12 of tibia cut guide 10 of FIG. 1. Tibia guide body 12 can comprise bone-engaging body 90, pin block 92 and socket block 94. Tibia guide body 12 can be assembled with attachment block 96, bushings 98A, 98B, 98C and 98D and pins 100A and 100B.

Figure 5:
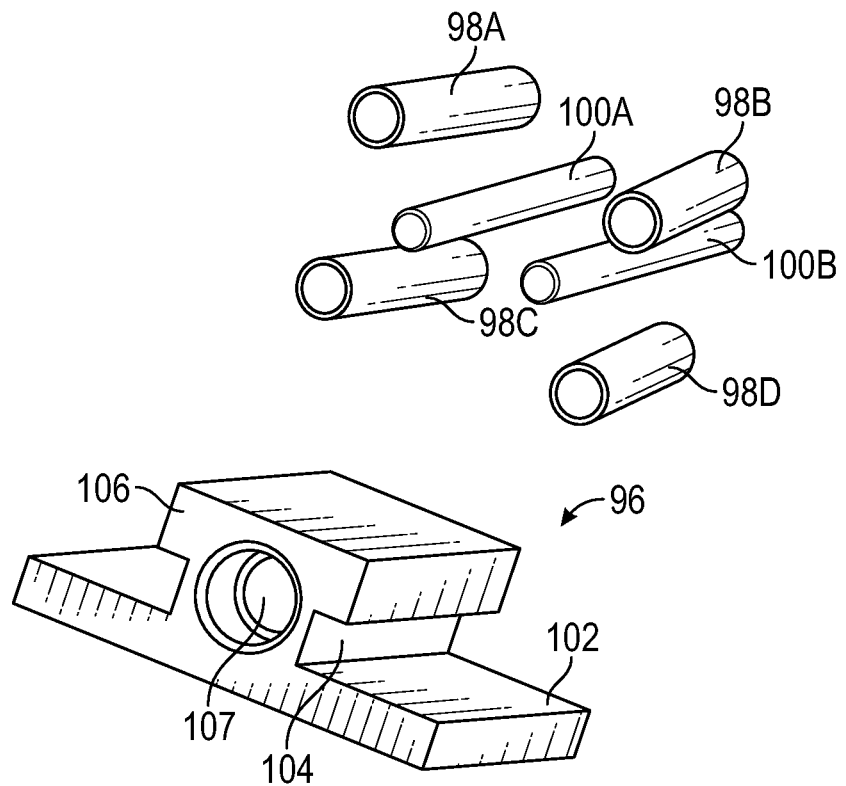
FIG. 5 is an exploded perspective view of hardware components used in the patient-specific tibia guide of FIG. 4.

FIG. 5 is an exploded perspective view of hardware components used in patient-specific tibia guide body 12 of FIG. 4. Bushings 98A-98D can comprise cylindrical bodies having bores extending therethrough to, for example, receive guide pins. Bushings 98A-98D can be made of a hard material, such as metal (e.g., stainless steel), to prevent damage to bone-engaging body 90 by the guide pins, so as to avoid producing any shavings of material of bone-engaging body 90 that can become loosened within the patient. Pins 100A and 100B can comprise solid dowel pins. Pins 100A and 100B can have circular cross-sections and can be made of radiopaque material for viewing in imaging, such as x-ray images. As such, pins 100A and 100B can be used to verify orientation of tibia guide body 12 in imaging of anatomy of a patient, as discussed below.

Attachment block 96 can comprise base 102, neck 104, support 106 and bore 107. Attachment block 96 can be shaped to fit within a correspondingly shaped socket (see socket 120 of FIG. 6A) within bone-engaging body 90.

FIGS. 6A, 6B, 6C and 6D are front, side, back and perspective views of patient-specific tibia guide body 12 of FIG. 4 with the hardware of FIG. 5 removed.

Pin block 92 can comprise bores 108A-108D, bores 110A and 110B, channel 112 and flanges 114A and 114B.

Socket block 94 can comprise extension 116, housing 118 socket 120 and cut flange 122. Bone-engaging body 90 can include cut opening 124, mount opening 126 and pin openings 128A and 128B.

Bone-engaging body 90 can comprise patient-specific surface 91 that can be irregularly shaped to mate and conform to the contours of the specific patient of tibia Tb, as can be determined from three-dimensional modeling of the specific patient obtained pre-operatively.

Figure 6A:
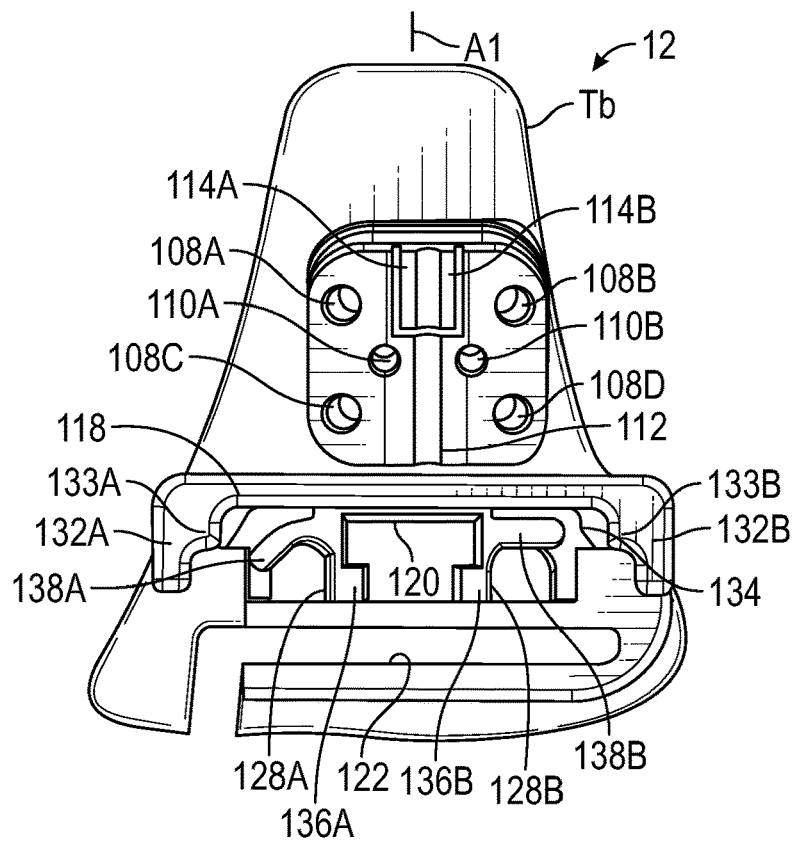
FIGS. 6A, 6B, 6C and 6D are front, side, back and perspective views of the patient-specific tibia guide body of FIG. 4 with the hardware of FIG. 5 removed.
Figure 6B:
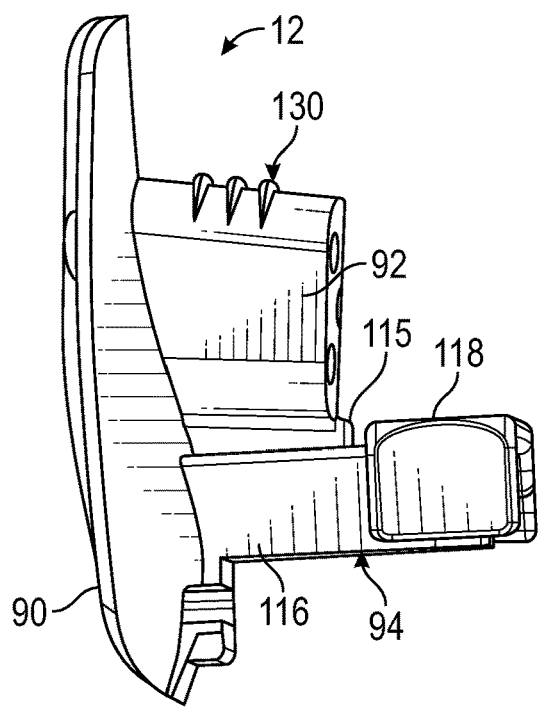
Figure 6C:
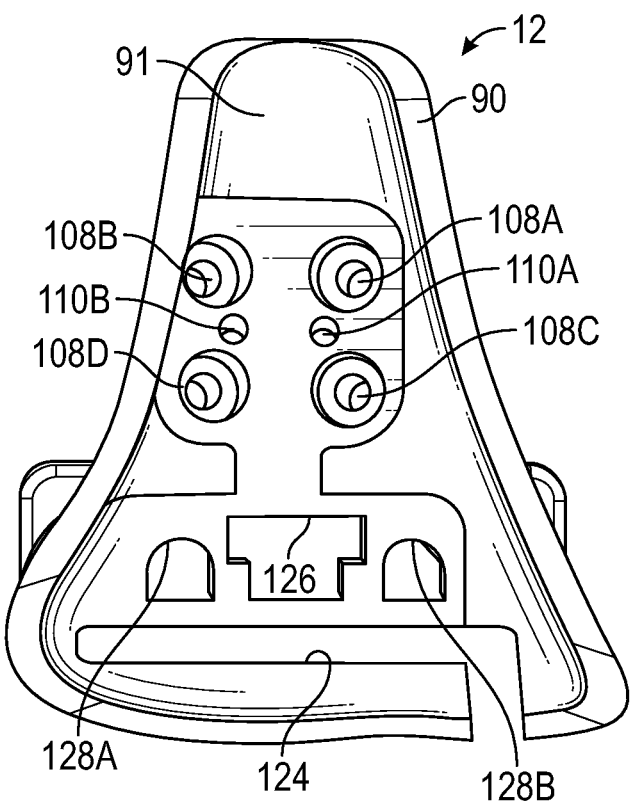
Figure 6D:
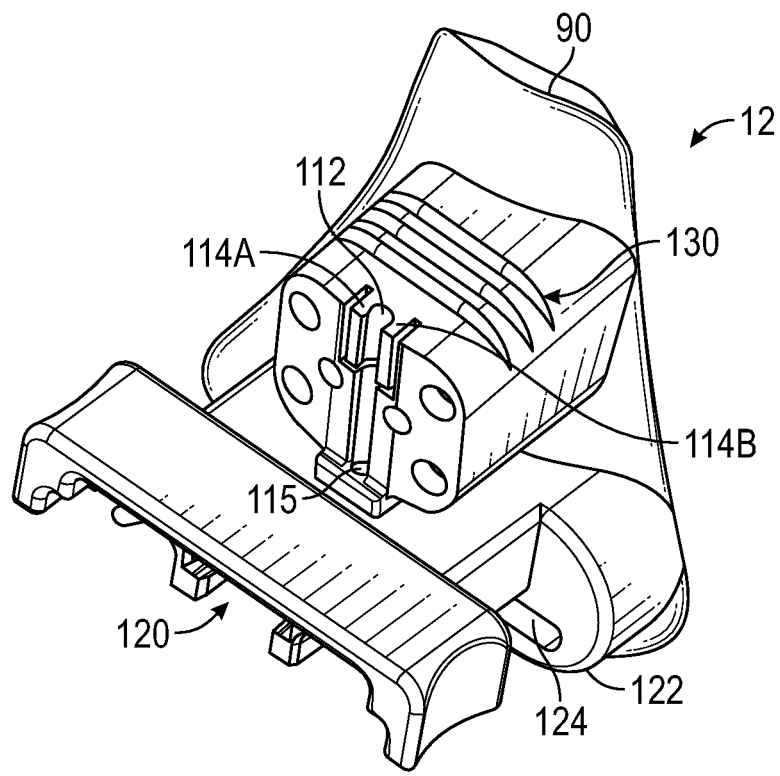

As can be seen in FIG. 6A, bores 108A-108D comprise openings into which bushings 98A-98D can be inserted. Bushings 98A-98D can be press-fit into bores 108A-108D and can be configured to not be removed manually from pin block 92. Pin block 92 can comprise bores 110A and 110B into which dowel pins 98A and 98B can be inserted. Dowel pins 98A and 98B can be press-fit into bores 110A and 110B and can be configured to not be removed manually from pin block 92.

Pin block 92 can include channel 112 for receiving alignment pin 18 of FIG. 1. Channel 112 can extend along axis A1, the orientation of which relative to bone-engaging body 90 can be determined pre-operatively based on images of tibia Tb. Flanges 114A and 114B can be configured to partially wrap around alignment pin 18 to secure pin 18 within channel 112. Base 115 can be provided between pin block 92 and extension 116 and can form a rest point for pin 18 (FIG. 1). Sidewalls of pin block 92 can be aligned parallel with channel 112 and channel 112 can be centered in pin block 92 to facilitate visualization of alignment of pin 18 in channel 112 with tibia Tb. Pin block 92 can additionally include grip features 130, such as ridges, to facilitate grasping of tibia guide 12.

Socket block 94 can comprise structure for receiving attachment block 96 and aligning attachment block 96 with channel 112. Extension 116 can project from bone-engaging body 90 underneath pin block 92. Extension 116 and pin block 92 can be attached to each other. Housing 118 can project laterally from extension 116 beyond the width of cut opening 124. Flanges 132A and 132B can extend downward from housing 118 to provide alignment of attachment block 96 with mount opening 126 and to provide surfaces for grasping tibia guide 12. The exterior of flanges 132A and 132B can be shaped or contoured to provide grasping surfaces, such as by being arcuately curved relative to axis A1 to facilitate pushing and pulling of tibia guide 12 against and away from tibia Tb. The interior of flanges 132A and 132B can include corners 133A and 133B, respectively, that facilitate alignment of tibia resection block 14, as discussed below.

Socket 120 can extend from back wall 134 adjacent bone-engaging body 90 to flush, or nearly flush, with the front of housing 118. Socket 120 can coincide with mount opening 126 that passes through bone-engaging body 90. Socket 120 can include flanges 136A and 136B to narrow the width of socket 120 thereat. Support 106 of attachment block 96 (FIG. 5) can be inserted into socket 120 such that neck 104 engages flanges 136A and 136B. The thickness of flanges 136A and 136B can be approximately equal to, of slightly less than, the height of neck 104 to allow attachment block 96 to be inserted into socket 120, such as with a force-fit or interference-fit.

Figure 6E:
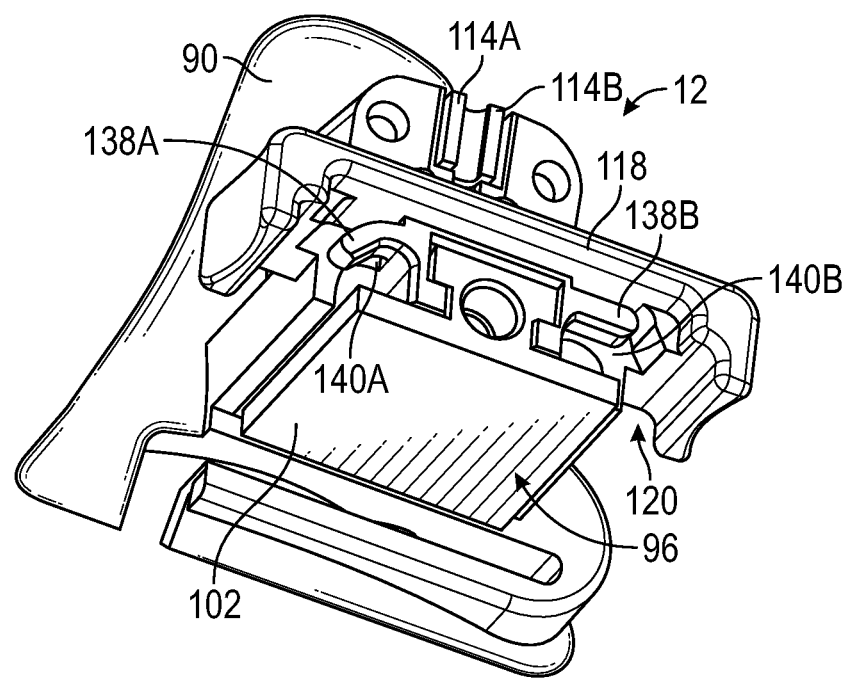
FIG. 6E is bottom perspective view of the patient-specific tibia guide body of FIG. 4 with the hardware installed.
Figure 6F:
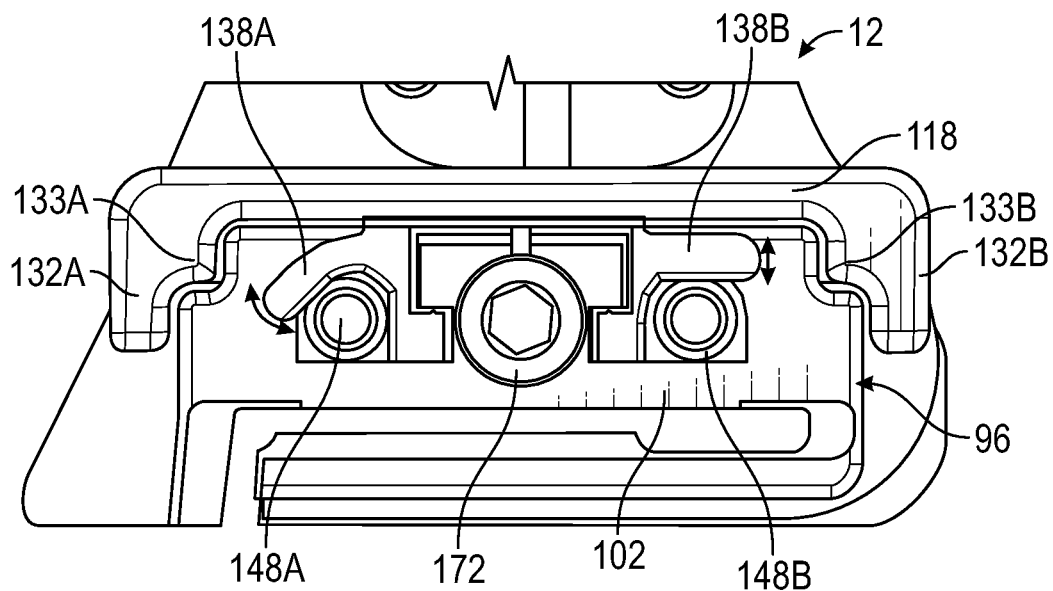
FIG. 6F is a schematic view of the patient-specific tibia guide body with a tibia resection block attached thereto.

Pin openings 128A and 128B can extend through bone-engaging body 90 within socket 120. As can be seen in FIG. 6E, socket 120 can further comprise biasing elements 138A and 138B. Biasing elements 138A and 138B can be used to position attachment block 96 within socket 120. Biasing elements 138A and 138B are spaced from back wall 134 and therefore form notches 140A and 140B within socket 120. As such, biasing elements 138A and 138B can be cantilevered and can comprise tensioning members that push against tibia resection block 14, as can be seen in FIG. 6F and which is discussed further below with reference to FIG. 7A-7D.

FIGS. 7A, 7B, 7C and 7D are front side top and perspective views of tibia resection block 14 for use with patient-specific tibia guide body 12 of FIG. 4. Tibia resection block 14 can comprise anterior panel 142, inferior panel 144, side panel 146, first pin boss 148A, second pin boss 148B and fastener 150.

Anterior panel 142 can comprise notches 152A and 152B for engaging corners 133A and 133B (FIG. 6A). Anterior panel 142 can be a planar body having posterior surface 154 for engaging biasing elements 138A and 138B of socket 120. Inferior surface 156 of anterior panel 142 can comprise a cutting guide surface that forms a portion of cutting guide slot 158 along with top surface 160 of inferior panel 144.

Inferior panel 144 can be a planar body having superior surface 162 that can extend back toward cut flange 122 (FIG. 6A) and align with cut opening 124 of bone-engaging body 90. As such, superior surface 162 can comprise an elongate cutting guide surface against which a cutting instrument, such as a saw blade can rest, slide, oscillate or reciprocate. Inferior panel 144 can additionally include trough 163 to facilitate insertion of pins and cutting instruments within cutting guide slot 158, as discussed in greater detail below with reference to FIG. 17.

Side panel 146 can extend down from anterior panel 142 past inferior panel 144. Side panel 146 can comprise side surface 164 that can comprise a cutting guide surface. In examples, inferior surface 156 and superior surface 160 can be parallel to each other and side surface 164 can be angled relative to surfaces 156 and 160.

Pin bosses 148A and 148B can extend from posterior surface 154 of anterior panel 142. Pin bosses 148A and 148B can comprise cylindrical bodies forming through-bores. Pin bosses 148A and 148B can align with bores 166A and 166B extending through anterior panel 142. The axes of pin boss 148A and bore 166A and pin boss 148B and bore 166B can align respectively and the axes of bores 166A and 166B can be parallel. Furthermore, the axes of bores 166A and 166B can be parallel to surface 160. As discussed below, pin bosses 148A and 148B can engage biasing elements 138A and 138B to position resection block 14 within socket 120.

Figure 7A:
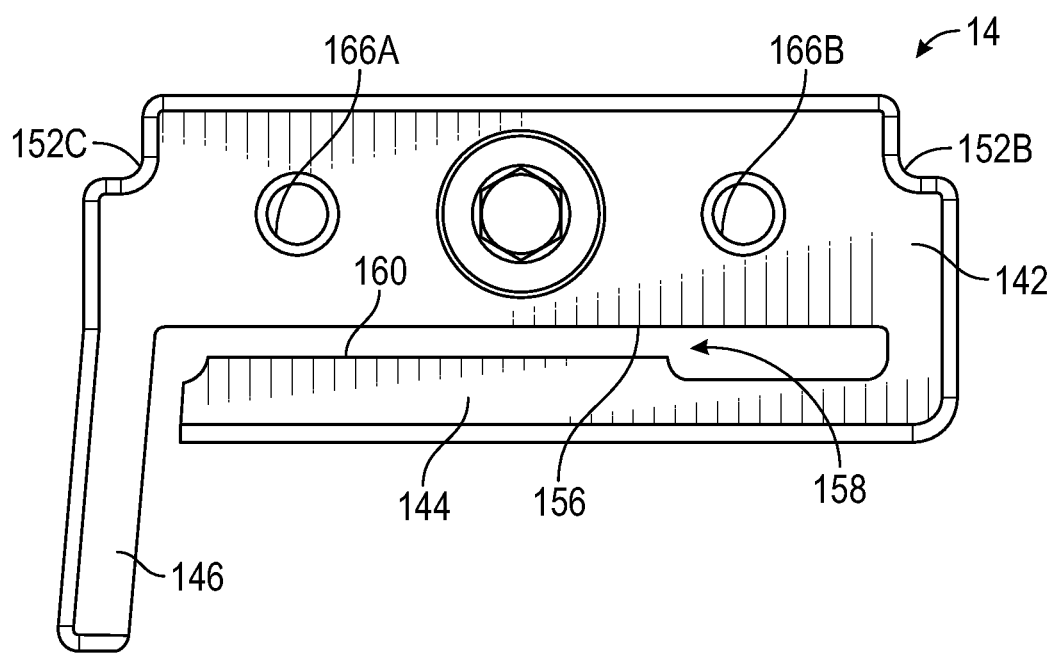
FIGS. 7A, 7B, 7C and 7D are front, side, top and perspective views of a tibia resection block for use with the patient-specific tibia guide body of FIG. 4.
Figure 7B:
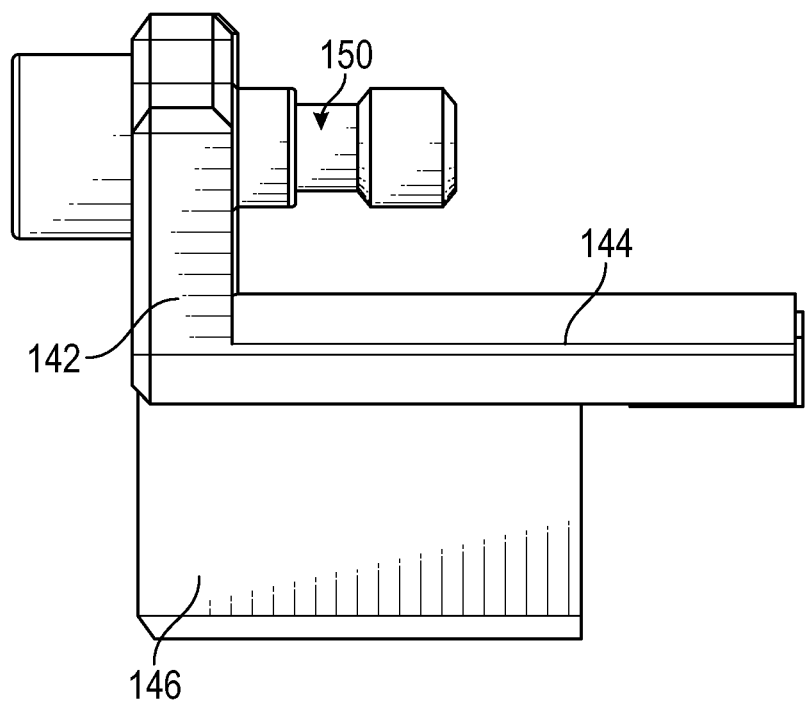
Figure 7C:
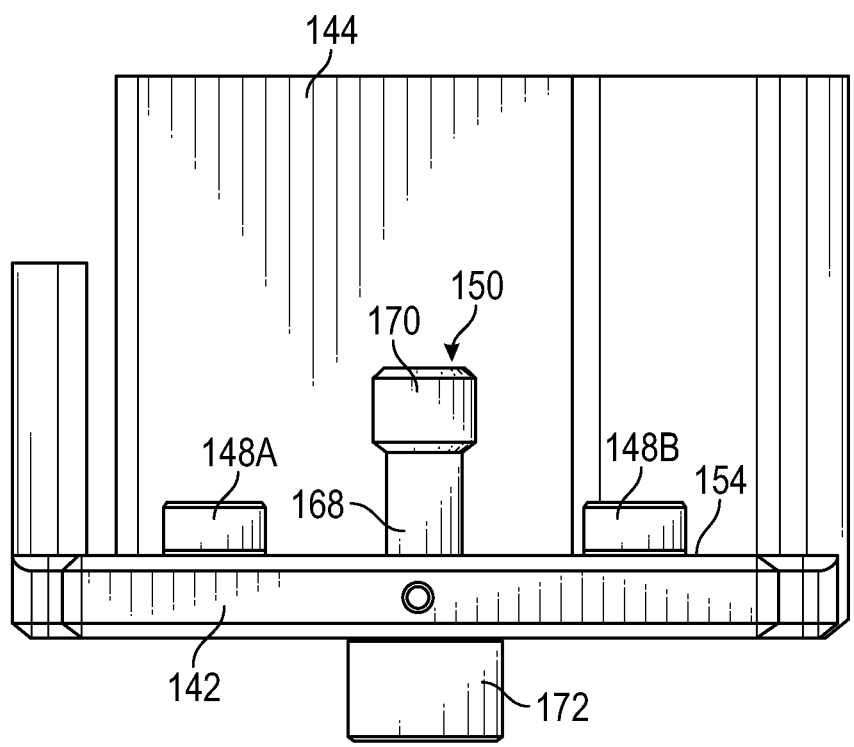
Figure 7D:
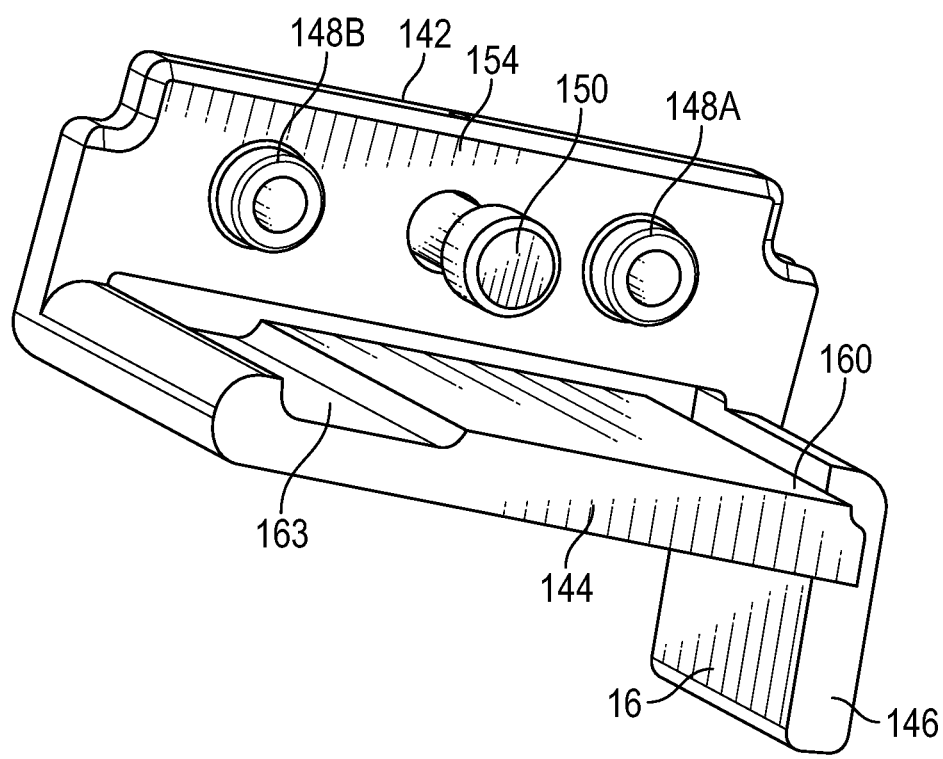

Fastener 150 can comprise a projection for engaging attachment block 96, such as at bore 107 (FIG. 5). Fastener 150 can comprise shaft 168, head 170 and knob 172. In examples, shaft 168 can extend through a bore within anterior panel 144 and knob 172 can be separately attached to shaft 168. Thus, fastener 150 can be rotatable within anterior panel 144, but can be immobilized with the use of a fastener or set-screw, as shown in FIG. 7C. Head 170 can comprise a threaded body integral with shaft 168 for coupling to bore 107, which, in examples, can be complimentarily threaded for engagement with thread on head 170. Knob 172 can include a hex socket, or some other torque transferring engagement, to receive a tool for rotating fastener 150 to facilitate coupling of head 170 with bore 107.

With reference to FIG. 6F, when attachment block 96 is seated in bone-engaging body 90 and tibia resection block 14 is seated within housing 118 that forms part of socket 120, biasing elements 138A and 138B can engage pin bosses 148A and 148B, respectively. In particular, biasing elements 138A and 138B can push against pin bosses 148A and 148B to push tibia resection block 14 against base 102 (FIG. 5). Biasing element 138A can be curved to project laterally outward from socket 120 and then downward toward cut flange 122. As such, biasing element 138A can push pin boss 148A down against base 102 and inward against flange socket 120 proximate flange 136A. Biasing element 138B can be straight to project laterally straight from socket 120.

As such, biasing element 138B can push pin boss 148B down against base 102. Thus, biasing elements 138A and 138B can be configured to remove free-play and prevent rotation of tibia resection block 14 to more repeatably position tibia resection block 14 relative to bone-engaging body 90 to allow for more precise resections.

FIGS. 8A, 8B, 8C and 8D are front, side, top and perspective views of patient-specific talus guide body 32 of talus cut guide 14 of FIG. 2. Guide body 32 can comprise bone-engaging body 180, socket block 182, anchor body 184 and locking device 186. Talus guide body 32 can be assembled with dowel pins 188A and 188B.

Figure 8A:
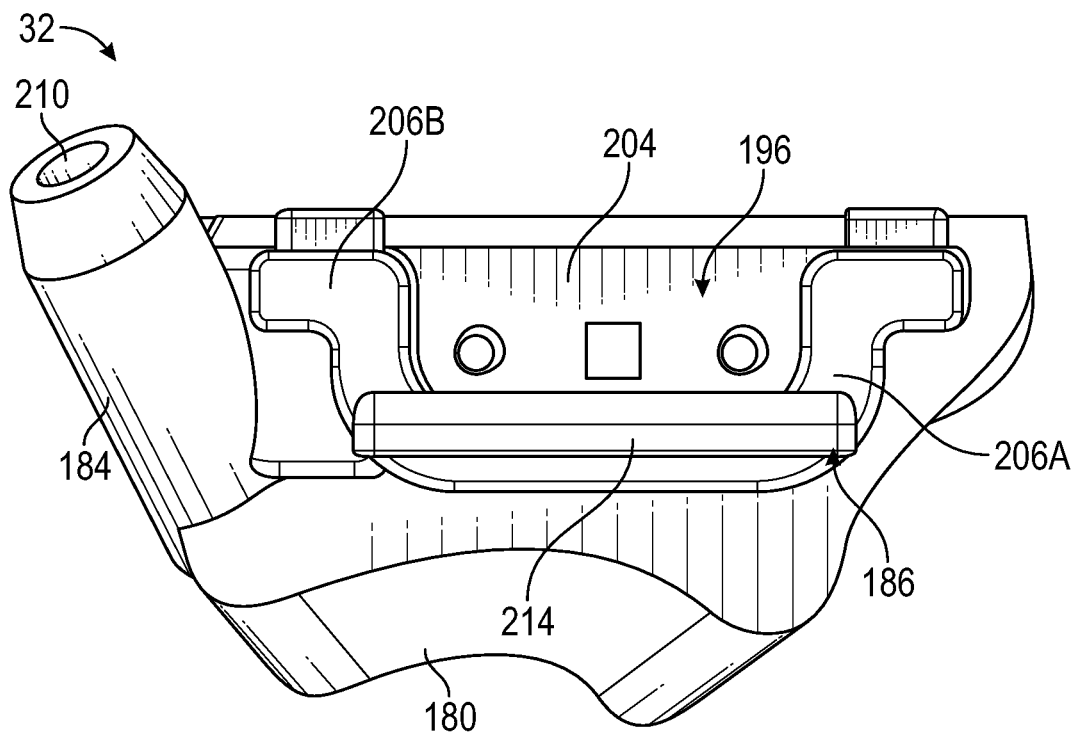
FIGS. 8A, 8B, 8C and 8D are front, side, top and perspective views of a patient-specific talus guide body of the talus cut guide of FIG. 2.
Figure 8B:
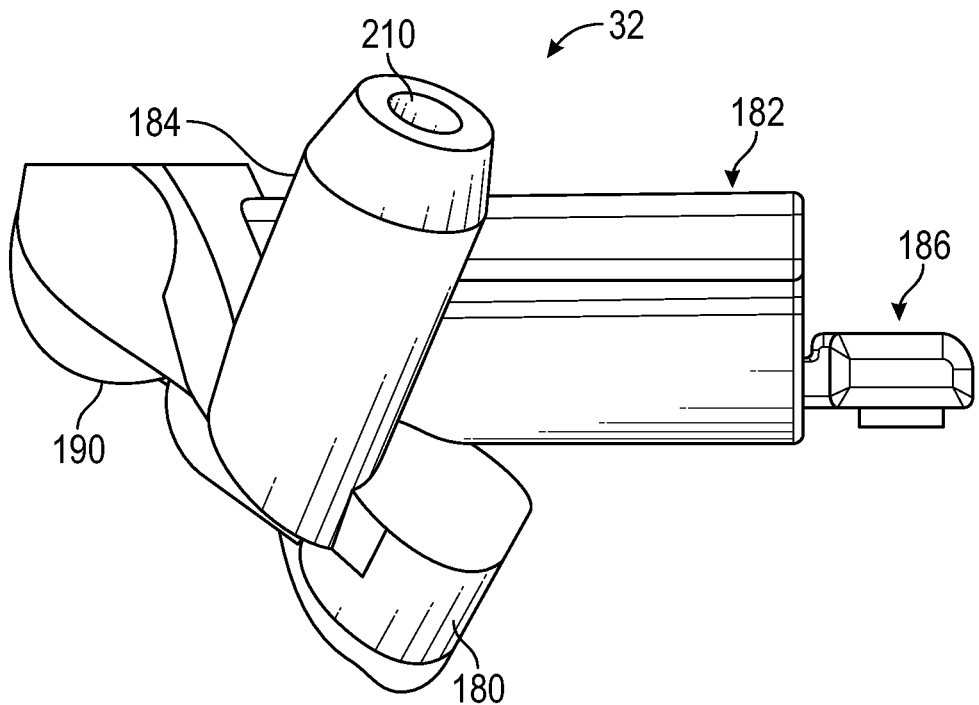
Figure 8C:
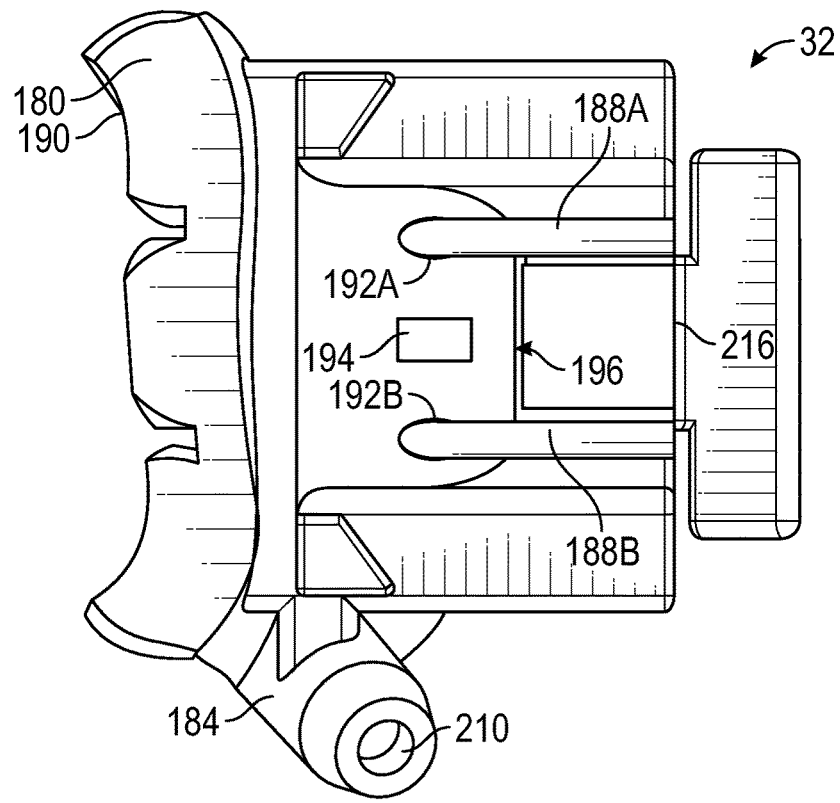
Figure 8D:
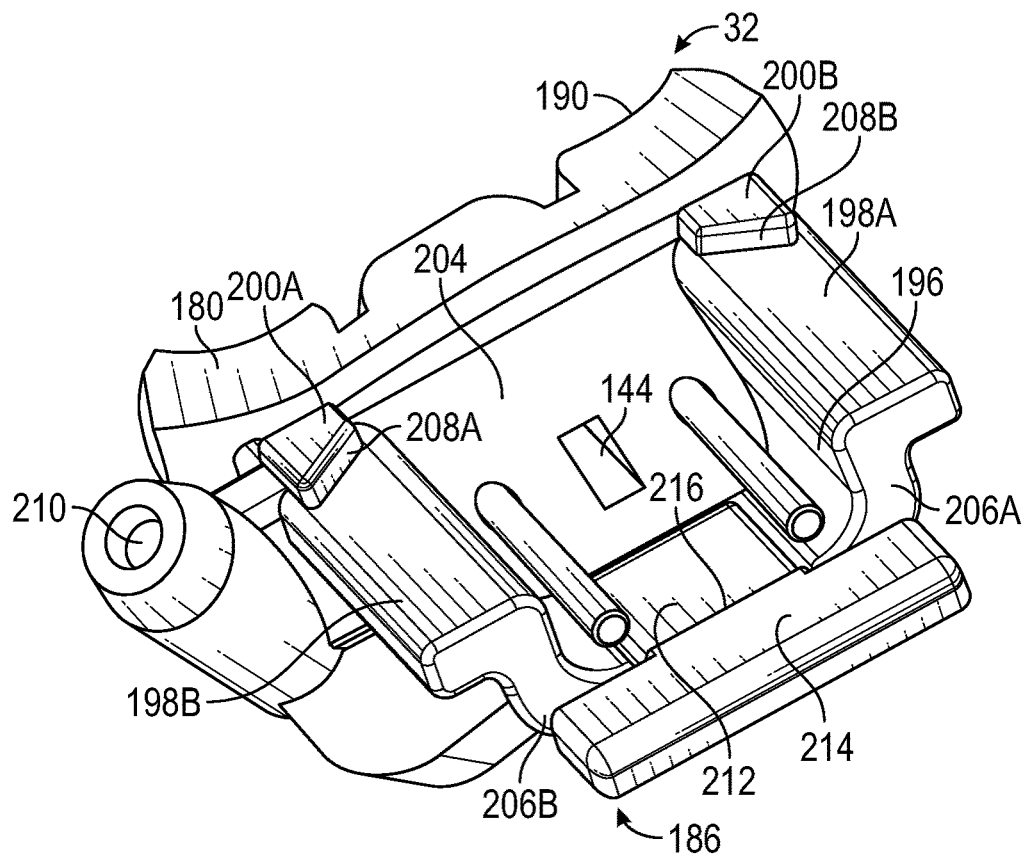
Figure 8E:
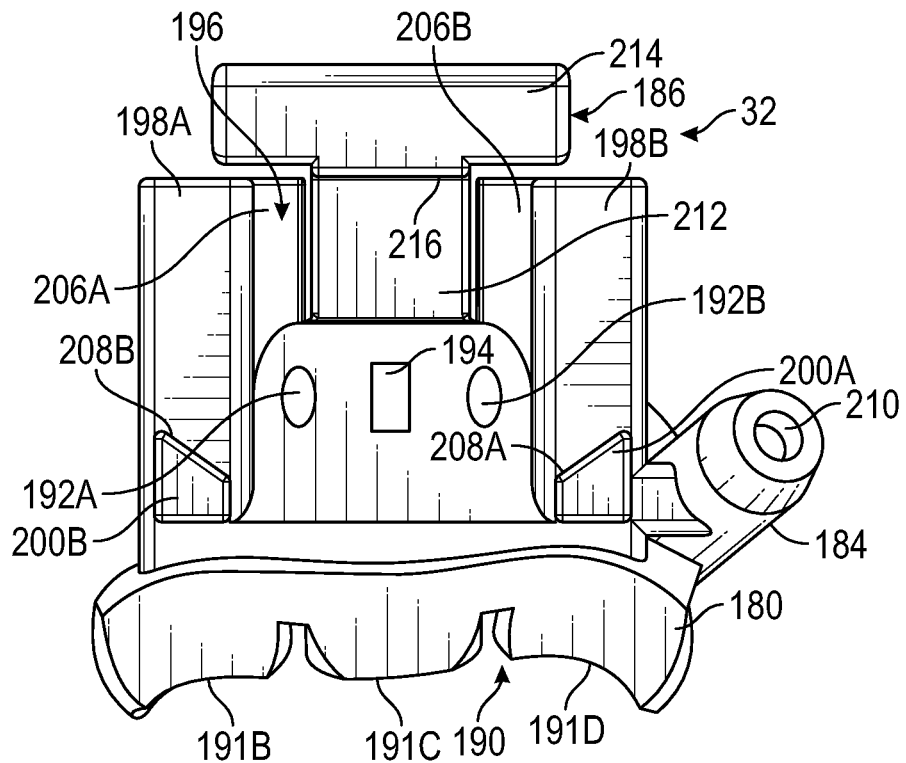
FIG. 8E is a top view of the patient-specific talus guide body of FIGS. 8A-8D with dowel pins removed to show a locking mechanism.
Figure 8F:
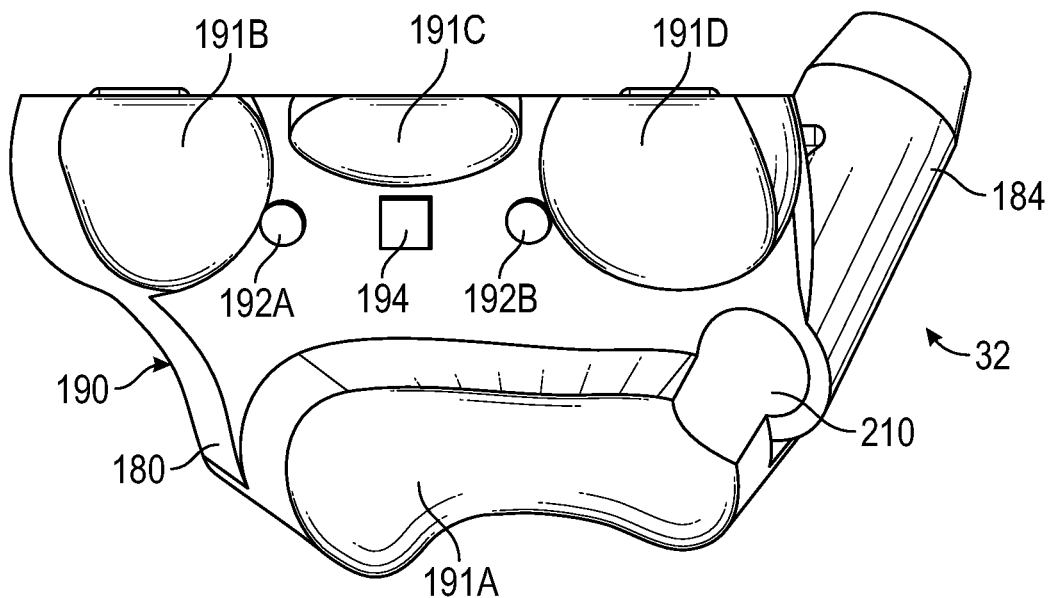
FIGS. 8F and 8G are rear and bottom views of the patient-specific talus guide body of FIG. 8E showing patient-specific contact surfaces.
Figure 8G:
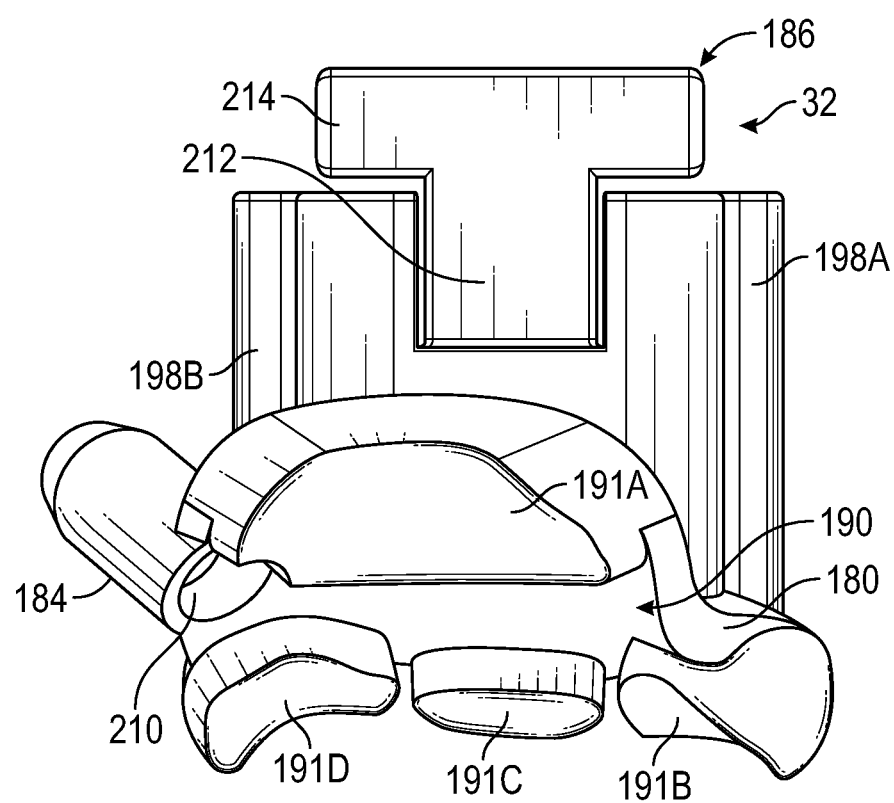

Bone-engaging body 180 can comprise patient-specific surface 190 that can be irregularly shaped to mate and conform to a specific patient's bone contour. As can be seen in FIGS. 8F and 8G, patient-specific surface 190 can include pads 191A, 191B, 191C and 191D. Pads 191A-191D can comprise patient-specific surface 91 that can be irregularly shaped to mate and conform to the contours of the specific patient of talus Tl, as can be determined from three-dimensional modeling of the specific patient obtained pre-operatively.

Bone-engaging body 180 can comprise bores 192A and 192B for receiving dowel pins 188A and 188B. Bores 192A and 192B can extend completely through bone-engaging body 180 and socket block 182 and can extend parallel to each other to facilitate sliding of talus resection block 34. Dowel pins 188A and 188B can be press-fit into bores 192A and 192B and can be configured to not be removed manually from bone-engaging body 180. Bone-engaging body 180 can additionally include channel 194 that can permit passage of a guide pin, such as pin 46 (FIG. 2) through bone-engaging body 180 between bores 192A and 192B.

Socket block 182 can comprise inferior cup 196, sidewalls 198A and 198B and stops 200A and 200B. Inferior cup 196 can provide a socket for receiving talus resection block 34 and can include posterior portion 204 against bone-engaging body 180 and sloped portions 206A and 206B for supporting the underside of talus resection block 34. Sloped portions 206A and 206B can face locking device 186. Sidewalls 198A and 198B can extend laterally outward from inferior cup 196 to provide planar surfaces for supporting talus resection block 34. Stops 200A and 200B can extend superiorly from sidewalls 198A and 198B and can abut bone-engaging body 180. Stops 200A and 200B can include angled engagement surfaces 208A and 208B that angle toward pins 188A and 188B and are perpendicular to surfaces 198A and 198B. Angled engagement surfaces 208A and 208B can form acute angles with axes of pins 188A and 188B, respectively. Angled engagement surfaces 208A and 208B can be centered on inferior cup 196.

Anchor body 184 can comprise a projection extending from bone-engaging body 180 to receive a guide pin, such as pin 42 (FIG. 2), for anchoring talus cut guide 30 to talus Tl. In examples, anchor body 184 can comprise a cylindrical element projecting from bone-engaging body 180 adjacent socket block 182. Anchor body 184 can include bore 210 to receive anchor pin 42 (FIG. 2). Bore 210 can be oriented to avoid placing pin 42 in the trajectory of a cut plane and at an angle to secure bone-engaging body 180. Bore 210 can be oblique to a central axis of channel 194 to inhibit rotation of talus guide body 32 relative to talus Tl.

Figure 21:
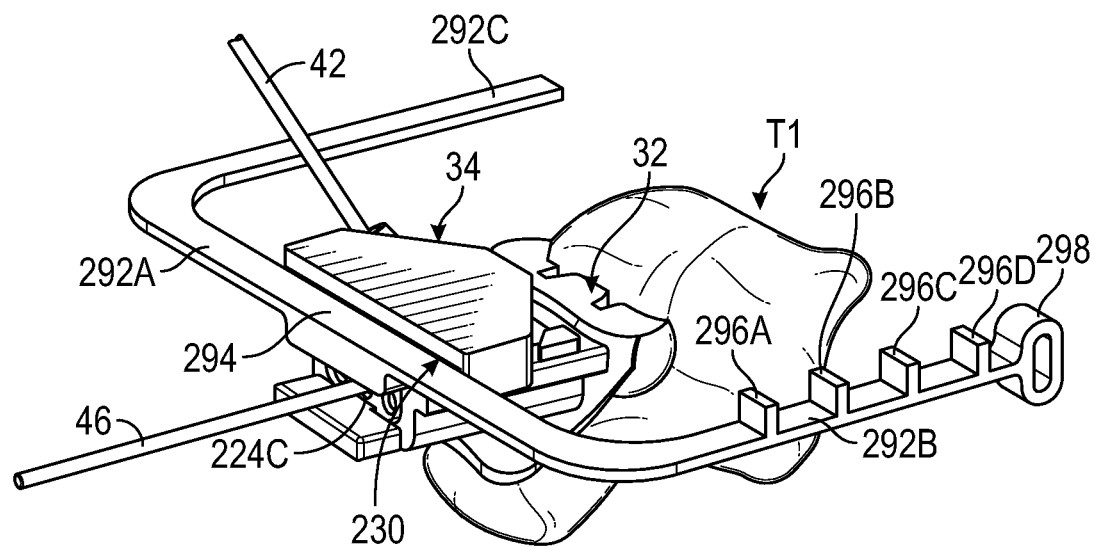
FIG. 21 is a perspective view of a talus stylus inserted into the talus resection block of the assembly of FIG. 20.

Locking device 186 can comprise features for securing talus resection block 34 within socket block 182. Locking device 186 can comprise a resilient or biased element that resists movement of talus resection block 34 out of socket block 182. In examples, locking device 186 can comprise cantilevered body 212 and projection 214. Cantilevered body 212 can extend anteriorly from posterior portion 204 to the anterior faces of sloped portions 206A and 206B and can act as a spring to secure talus resection block 34. As can be seen in FIG. 8E, cantilevered body 212 is spaced from sloped portions 206A and 206B so that cantilevered body 212 can flex. Projection 214 can extend anteriorly from cantilevered body 212 and superiorly relative to cantilevered body 212. As such, projection 214 can form lip 216 that can engage an anterior surface of talus resection block 34, as can be seen in FIGS. 2 and 21.

FIGS. 9A, 9B, 9C and 9D are front, side, bottom and perspective views of talus resection block 34 for use with patient-specific talus guide body 32 of FIGS. 8A-8G. Talus resection block 34 can comprise coupling block 220 and resection guide block 222. Coupling block 220 can comprise bores 224A, 224B and 224C, anterior surface 225, posterior surface 226 and curved sides 228A and 228B. Resection guide block 222 can comprise slot 230, superior surface 231, guide surface 232, anterior surface 233, troughs 234A and 234B and angled engagement surfaces 236A and 236B.

Bores 224A and 224B can be configured to receive dowel pins 188A and 188B, respectively. Bore 224C can be configured to receive pin 46 (FIG. 2). Posterior surface 226 can be configured to abut posterior portion 204 of socket block 182 of talus guide body 32. Curved sides 228A and 228B can be configured to engage sloped portions 206A and 206B, respectively, of inferior cup 196 of talus guide body 32. Thus, bores 224A and 224B can be slid around dowel pins 188A and 188B to seat coupling block 220 within socket block 182 to couple talus resection block 34 to talus guide body 32. With coupling block 220 engaged with socket block 182, resection guide block 222 can be positioned above sloped portions 206A and 206B such that angled engagement surfaces 236A and 236B contact angled engagement surfaces 208A and 208B of stops 200A and 200B. Mating of angled engagement surfaces 236A and 236B with angled engagement surfaces 208A and 208B can help ensure alignment of talus resection block 34 with talus guide body 32 such that slot 230 is aligned relative to patient-specific surface 190. Slot 230 can thus be properly oriented relative to talus Tl such that a cutting instrument can be positioned against surface 232 to squarely engage talus Tl. Troughs 234A and 234B can be provided in slot 230 to facilitate entry of cutting instruments and guide pins in slot 230.

Figure 10A:
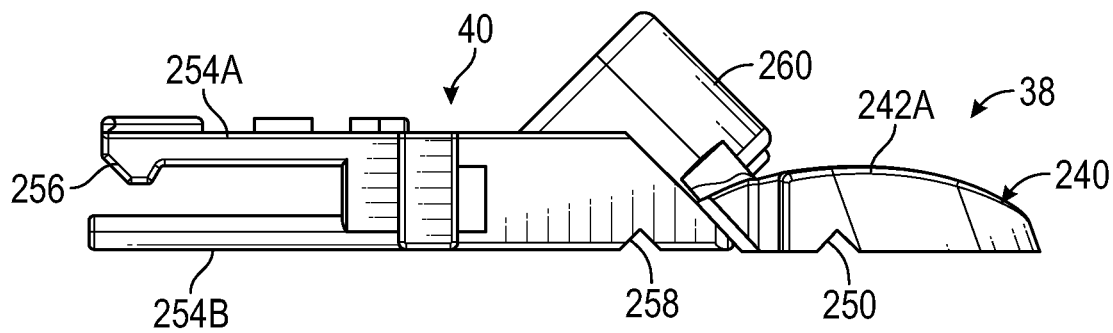
FIGS. 10A, 10B and 10C are side, top and bottom views of floating talar trial assembled with a floating talar guide.
Figure 10B:
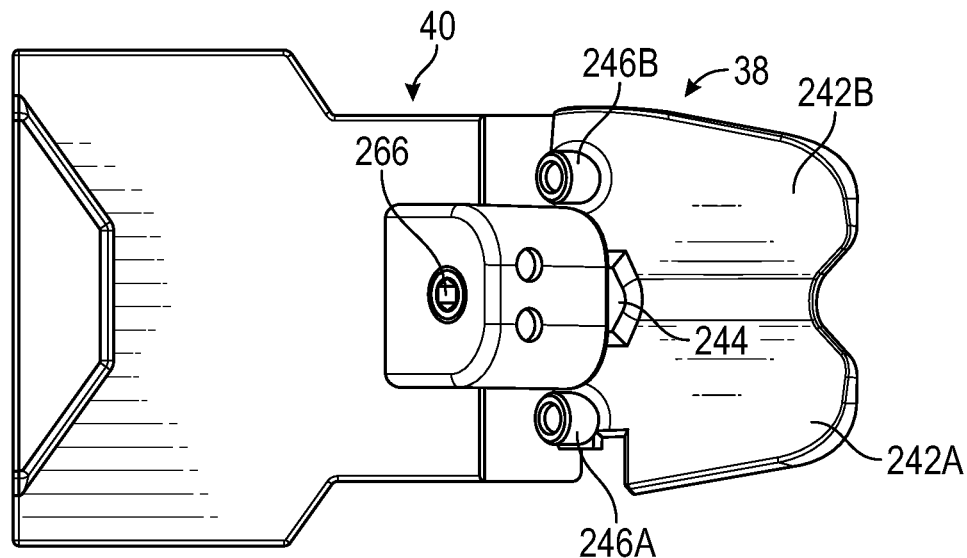
Figure 10C:
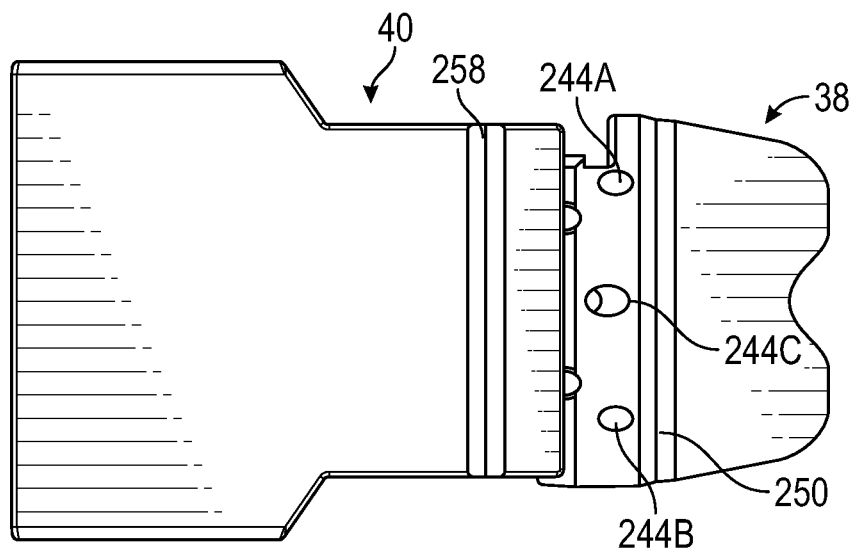

FIGS. 10A, 10B and 10C are top, side and bottom views of floating talar trial 38 assembled with floating talar guide 40. FIG. 10D is an exploded perspective top view of the assembly of floating talar trial 38 and floating talar guide 40 of FIGS. 10A-10C. FIG. 10E is an exploded perspective bottom view of the assembly of floating talar trial 38 and floating talar guide 40 of FIGS. 10A-10C. FIGS. 10A-10E are discussed concurrently.

Floating talar trial 38 can comprise trial body 240, first condyle 242A, second condyle 242B, bores 244A, 244B and 244C, collars 246A and 246B, socket 248, inferior surface 249, first indicator notch 250 and engagement face 251.

Floating talar guide 40 can comprise interface body 252, first flange 254A, second flange 254B, lip 256, inferior surface 257, second indicator notch 258, engagement face 259, fastener block 260 and fastener bore 262.

Floating talar trial 38 and floating talar guide 40 can be coupled together using fastener 264, which can comprise head 266, shaft 268 and threaded portion 270.

Talar trial 38 and talar guide 40 can be considered to float against resected surface 302 (FIG. 24) when coupled to patient-specific talus guide 32 via talus cut guide 34, as discussed below with reference to FIGS. 27 and 28. Talus guide 32 combined with talus resection block 34 as well as talar guide 40 and floating talar trial 38 define the orientation and the position of the anterior resected surface of Talus Tl.

FIGS. 11-35 illustrate an example method of performing a total-ankle arthroplasty procedure. Description of FIGS. 11-35 show particular steps of a method, any of which may be skipped or performed out of order from the sequence described. The method describes a procedure for implanting prosthetic ankle device 60 of FIGS. 3A-3D, though other prosthetic devices and systems may be implanted with the instruments, devices and procedures described herein.

Figure 11:
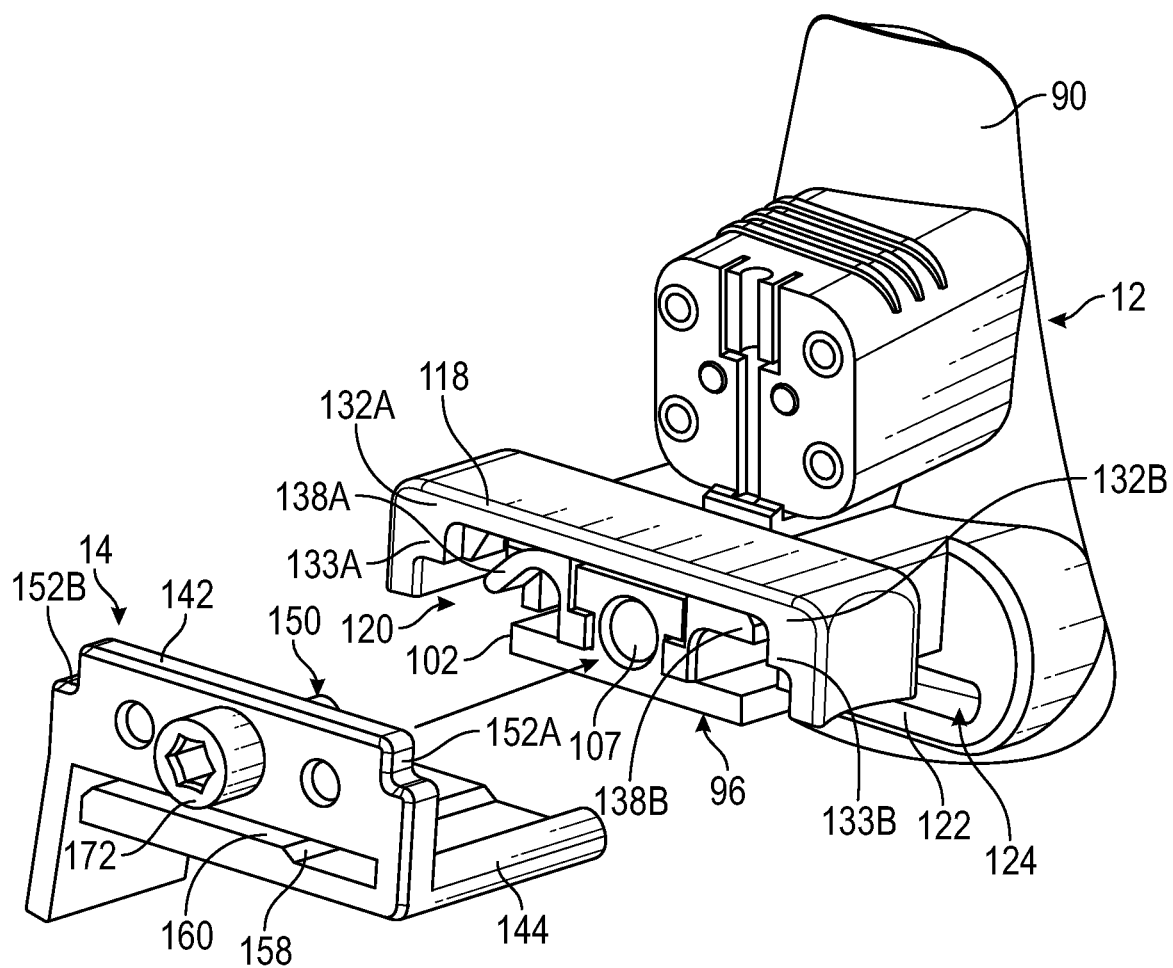
FIG. 11 is a perspective view of the tibia resection block of FIGS. 7A-7D being assembled with the patient-specific tibia guide body of FIG. 4.

FIG. 11 is a perspective view of tibia resection block 14 of FIGS. 7A-7D being assembled with patient-specific tibia guide body 12 of FIG. 4. Fastener 150 can be inserted into bore 107 of attachment block 96. In examples, head 170 can be threaded into bore 107. Knob 172 can be rotated to secure the threaded engagement with bore 107. Knob 172 can include a socket, such as a socket for a 3.5 hex driver, to facilitate rotation of fastener 150. Inferior panel 144 can be inserted underneath base 102. Anterior panel 142 can be pushed into housing 118 defining socket 120. Notches 152A and 152B of anterior panel 142 can receive corners 133A and 133B of flanges 132A and 132B, respectively, of housing 118. Further, with tibia resection block 14 seated within socket 120, biasing element 138A and 138B can push against pin bosses 148A and 148B, respectively, extending from the posterior side of anterior panel 142 to facilitate alignment of tibia resection block 14 with patient-specific tibia guide body 12, as described with reference to FIG. 6F. Inserted as such, superior surface 160 of cutting guide slot 158 can align with cut flange 122 defining cut opening 124. Further, bores 166A and 166B can align with pin openings 128A and 128B (FIGS. 6A and 6C), respectively, of tibia guide body 12.

Tibia resection block 14 can be configured in different sizes. Thus, a surgeon can be provided with a plurality of different tibia resection blocks 14, each having a different sized cutting guide slot 158. For example, a standard sized cutting block can be provided in addition to a large sized cutting block where cutting guide slot 158 is wider. The size of tibia resection block 14 selected for a specific patient can be determined pre-operatively per a surgical plan and can be based on imaging of the specific patient. The size of tibia resection block 14 can be indicated on the resection block itself and on patient-specific tibia guide body 12. The standard sized resection block will only fit with socket 120 produced for a such a resection block and indicia on tibia guide body 12 can indicate the size of socket 120. The surgical plan can be consulted to ensure the properly sized resection block and tibia guide body are selected. Note, the size of the resection block need not correspond to a size of prosthetic ankle device 60 selected for implantation.

Figure 12:
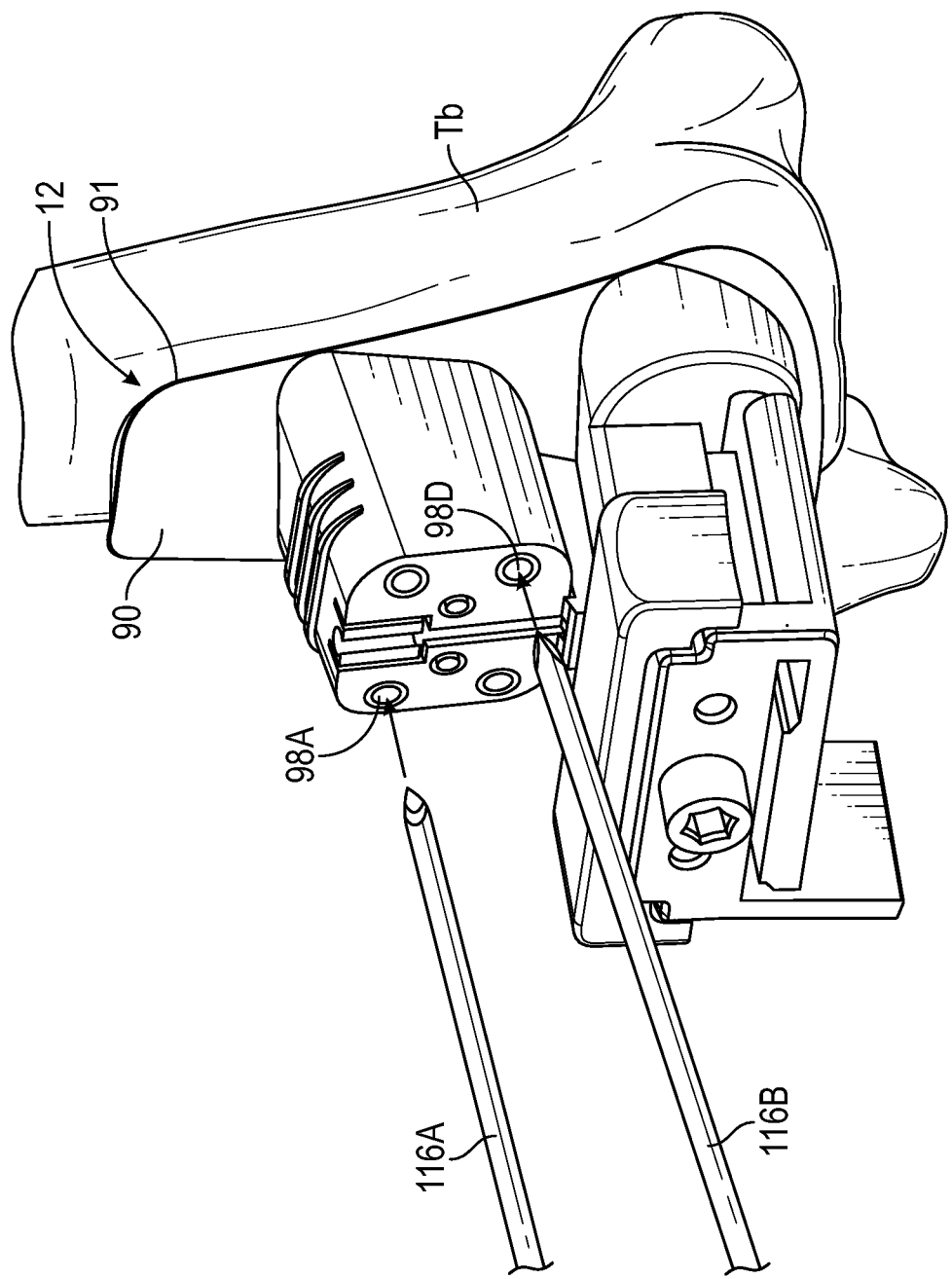
FIG. 12 is a perspective view of the assembly of FIG. 11 being fastened to an anterior side of a distal end of a tibia.

FIG. 12 is a perspective view of the assembly of FIG. 11 being fastened to an anterior side of a distal end of tibia Tb. Bone-engaging body 90 can be pushed against tibia Tb. Body 90 can be positioned proximally on the shaft of tibia Tb and slid inferiorly toward the ankle joint. More specifically, body 90 can be positioned against the diaphysis or metaphysis region of tibia Tb and slid down toward the distal epiphysis region of tibia Tb. Patient-specific surface 91 of body 90 can be mated with the epiphysis region of tibia Tb in a patient-specific manner such that contours and facets of patient-specific surface 91 can mate to particular surface features of Tb in only one way, thereby facilitating alignment of cut opening 124 with tibia Tb per the surgical plan. Contouring of flanges 132A and 132 can be engaged by fingers of a surgeon to facilitate handling of patient-specific tibia guide body 12. Likewise, grip feature 130 on pin block 92 can be engaged by a user to facilitate pushing of body 90 against tibia Tb. Body 90 will fit into place at the desired location to resect the distal end of tibia Tb to receive tibial bearing component 62. Pins 16A and 16B can be inserted into bushings 98A and 98D to lock body 90 into place against tibia Tb. More or fewer pins can be used, or a different combination of bushings can be used, depending on the patient and the judgement of the surgeon. To ensure adequate locking of body 90, two pins can be used in two of bushings 98A-98D that are opposite and diagonal to each other. In examples, pins 16A and 16B can comprise 2.4 mm×120 mm guide wires.

Figure 13:
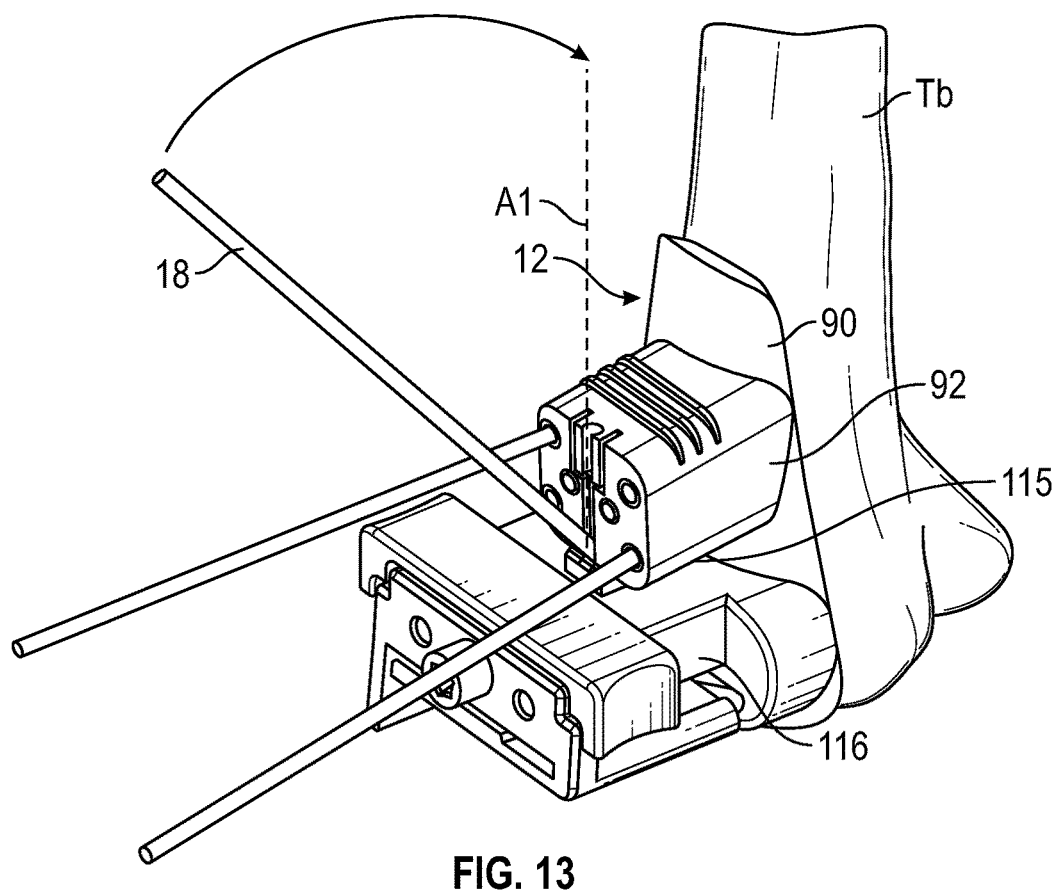
FIG. 13 is a perspective view of an alignment guide pin being inserted into an alignment slot of the assembly of FIG. 12.

FIG. 13 is a perspective view of alignment guide pin 18 being inserted into alignment channel 112 of the assembly of FIG. 12. In examples, pin 18 can comprise a 2.4 mm guide wire. An end of pin 18 can be pushed into engagement with base 115 and rotated on the end toward tibia Tb to be pushed between flanges 114A and 114B. Flanges 114A and 114B can deflect to receive pin 18 and relax to partially wrap around and hold pin 18. Thus, flanges 114A and 114B can comprise a snap-fit feature to ensure proper placement of and to retain pin 18. Flanges 114A and 114B can hold pin 18 along axis A1 (FIG. 6A). Axis A1 can be configured to extend along the mechanical axis of tibia Tb, such as by engagement of patient-specific surface 91 engaging tibia Tb. Orientation of cutting guide slot 158 can be set based off of axis A1 such that when pin 18 and axis A1 align with the mechanical axis of tibia Tb, the surgeon can know that cutting guide slot 158 will be properly aligned to produce a resection (e.g., resected surface 288A of FIG. 18) that will receive tibial bearing component 62. In examples, pin 18 and axis A1 will align cutting guide slot 158 to be perpendicular to the mechanical axis.

Figure 14:
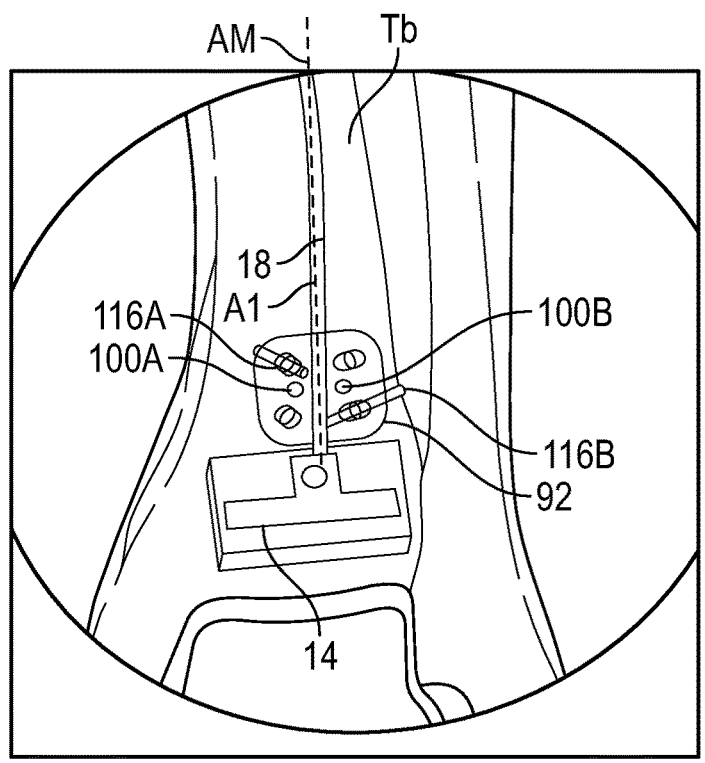
FIG. 14 is a schematic view of imaging of the alignment guide pin of FIG. 13 aligned with an axis of the distal portion of the tibia.

FIG. 14 is a schematic view of imaging of alignment guide pin 18 of FIG. 13 aligned with mechanical axis AM of the distal portion of tibia Tb. Imaging of tibia Tb in FIG. 14 can be taken in the frontal plane. In FIG. 14, resection block 14 is not shown on the fluoroscopic image, however attachment block 96 (FIG. 11) can be seen. In order for a surgeon to ensure that patient-specific tibia guide body 12 is properly mounted to and aligned with tibia Tb, images of tibia Tb with tibia guide body 12 can be obtained. For example, x-ray imaging or fluoroscopy imaging of tibia Tb can be obtained to view pin 18 extending relative to tibia Tb. Orientation of tibia guide body 12 can be confirmed by viewing ends of dowel pins 100A and 100B in the imaging. For example, each of pins 100A and 100B will appear as dots or circles if the imaging is producing a true anterior view perpendicular to the frontal plane. During a procedure, soft tissue of the patient will obstruct the diaphysis region of tibia Tb. The imaging can be used to view the cortical bone of tibia Tb relative to the full extent of pin 18. A surgeon can use judgment or refer to a surgical plan to verify that pin 18 aligns sufficiently, e.g., is parallel with, with mechanical axis AM.

Figure 15:
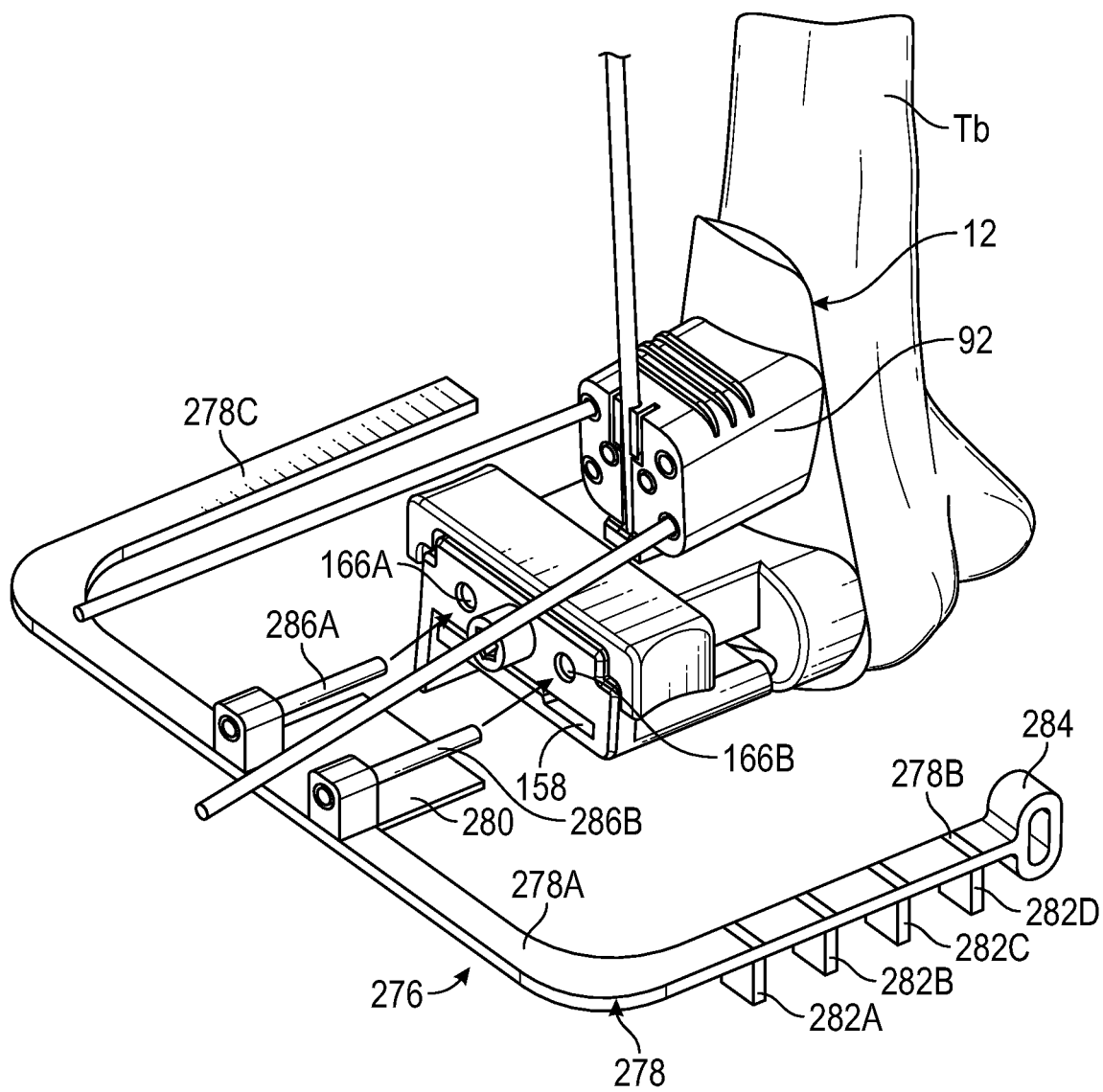
FIG. 15 is a perspective view of a tibial stylus being inserted into the tibia resection block of the assembly of FIG. 13.

FIG. 15 is a perspective view of tibial stylus 276 being inserted into tibia resection block 14 of the assembly of FIG. 13. Tibial stylus 276 can comprise u-shaped body 278, plate 280, fins 282A-282D, viewer 284 and pins 286A and 286B. Pins 286A and 286B can be inserted into bores 166A and 166B, respectively, contemporaneously with plate 280 being inserted into cutting guide slot 158. Pins 286A and 286B and plate 280 provide three points of contact between stylus 276 and tibia resection block 14 to ensure proper alignment of u-shaped body 278 with patient-specific tibia guide body 12.

U-shaped body 278 can comprise transverse extension 278A and sagittal arms 278B and 278C. Transverse extension 278A can be configured to extend medial-laterally beyond tibia Tb and soft tissue attached thereto to allow sagittal arms 278A and 278B to be positioned alongside tibia Tb. Arms 278A-278C can be configured to be co-planar such that when stylus 276 is viewed from the side, arms 278B and 278C can be behind each other. Fins 282A-282D can extend perpendicularly from arm 278B. Stylus 276 can be fabricated from a radiopaque material such that stylus 276 can be viewed in imaging, such as x-ray imaging.

Figure 16:
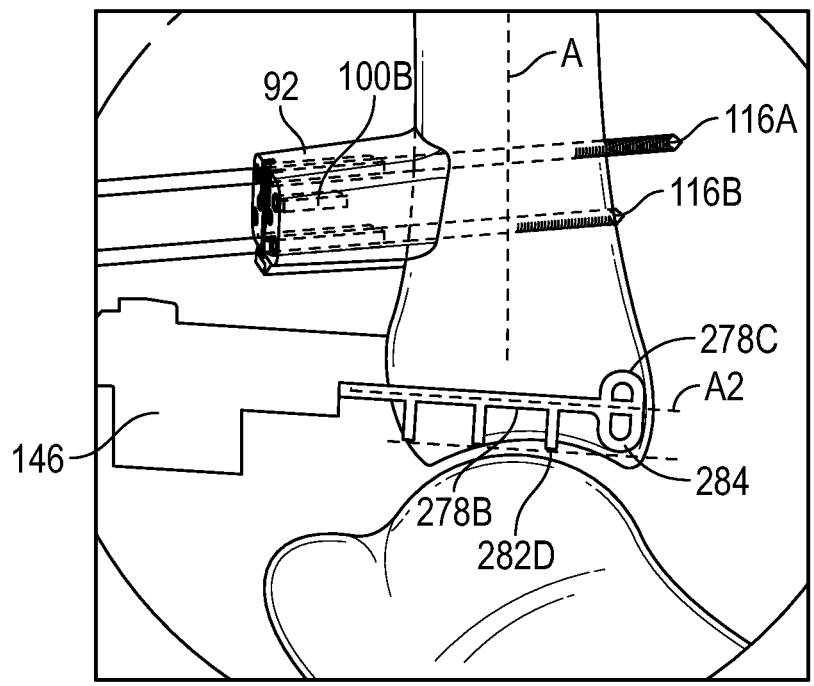
FIG. 16 is a schematic view of imaging of the tibial stylus of FIG. 15 indicating a resection height for the tibia.

FIG. 16 is a schematic view of imaging of tibial stylus 276 of FIG. 15 indicating a resection height or depth for tibia Tb. Imaging of FIG. 16 is taken from a medial-lateral side of patient-specific tibia guide body 12 in a lateral plane such that arm 278C is behind arm 278B. A distal portion of arm 278C can be viewed through an opening in viewer 284, which can comprise a targeting slot. As can be seen in FIG. 16, arms 278B and 278C extend in parallel. With arms 278A and 278C extending in parallel, a true view of the position of tibia guide body 12 along the length of mechanical axis AM can be observed. Thus, the amount of bone that is configured to be removed from the distal end of tibia Tb can be viewed. In particular, the perpendicular extension of fins 282A-282D can be seen. The length of fins 282A-282D can each correspond to a desired resection thickness of tibia Tb. In examples, fins 282A-282D can comprise tabs having lengths of 9 mm. Those of fins 282A-282D pointing to the most proximal portion of the distal end of tibia Tb indicate proper positioning of tibia resection guide body 12. In an example, the length of fins 282A-282D can represent the amount of bone appropriate for removal to implant tibial bearing component 62 and tibial tray component 64. As discussed, placement of tibia guide 10 along tibia Tb and hence placement of cutting guide slot 158 can be determined according to a pre-operative surgical plan. If fins 282A-282D indicate that too much or too little bone is to be removed per the installation of tibia guide body 12, the surgical plan can be altered or resection of tibia Tb can be performed using other instrumentation, such as non-patient-specific cutting guides.

Figure 17:
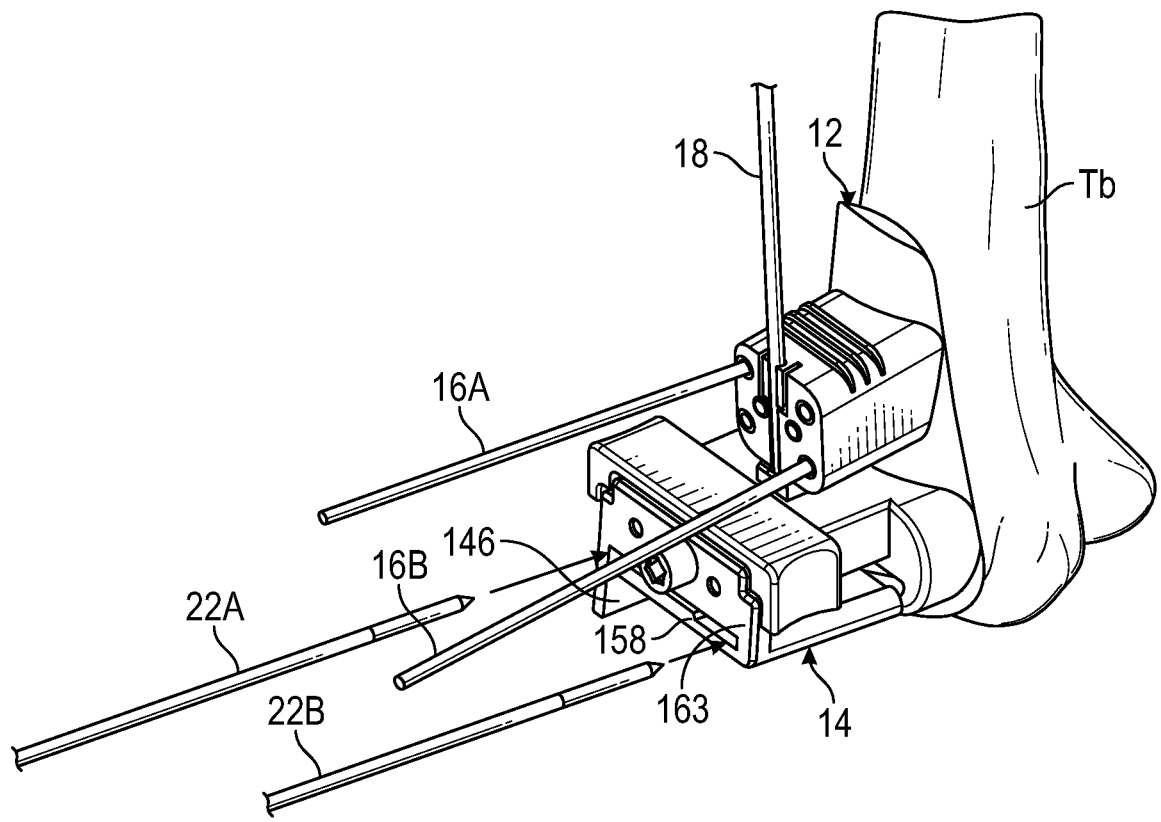
FIG. 17 is a perspective view of guide wires being inserted into a cutting slot of the tibia resection block of the assembly of FIG. 13.

FIG. 17 is a perspective view of pins 22A and 22B being inserted into cutting guide slot 158 of tibia resection block 14 of the assembly of FIG. 13. After orientation of tibia resection guide body 12 using stylus 276, stylus 276 can be removed and pins 22A and 22B can be inserted to prepare cutting guide slot 158 for receiving a cutting instrument. Trough 163 can be used to facilitate insertion of pin 22B. The gap between inferior panel 144 and side panel 146 can be used to facilitate insertion of pin 22A. In examples, pins 22A and 22B can comprise 2.4 mm guide wires. Pins 22A and 22B can be positioned at the medial and lateral extents of cutting guide slot 158 and can be used to shield portions of tibia resection guide body 12 and tibia Tb from the cutting instrument. In particular, pins 22A and 22B can shield portions of tibia resection guide body 12 that can be made of soft material, such as plastic. Additionally, pin 22A can be extend all the way into the syndesmotic gutter to protect the fibula and pin 22B can be positioned to protect the medial malleolus. With pins 22A and 22B in place, a cutting instrument can be inserted into cutting guide slot 158. In examples, a reciprocating or oscillating cutting or sawing blade can be slid against top surface 160 to ensure saw blade stability. Care should be taken to avoid damage postero-medially to the neurovascular bundle and centrally to the FHL tendon. Additionally, a cutting instrument can be guided along side panel 146 to resect along the medial malleolus.

After tibia Tb has been resected in two places along the distal end of tibia Tb and the medial malleolus, pins 22A and 22B can be removed. Next pins 16A and 16B can be removed to separate body 90 from tibia Tb. After tibia cut guide 10 has been removed, tibia Tb can be inspected to ensure that all excised bone has been removed.

Figure 18:
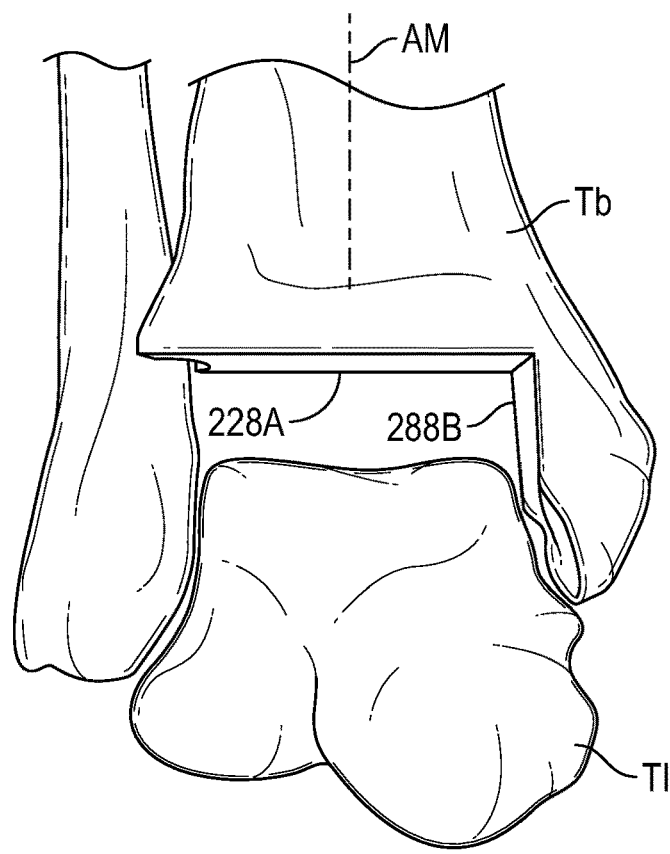
FIG. 18 is an anterior view of the tibia with the distal end and the medial malleolus resected to form planar surfaces.

FIG. 18 is an anterior view of tibia Tb with the distal end of tibia Tb and the medial malleolus being resected. The distal end is resected, such as by using cutting guide slot 158 to produce resected surface 288A and the medial malleolus is resected, such as by using side panel 146, to produce resected surface 288B. Resected surface 288A can be perpendicular to mechanical axis AM and resected surfaces 288B can be oblique to resected surfaces 288A.

Figure 19:
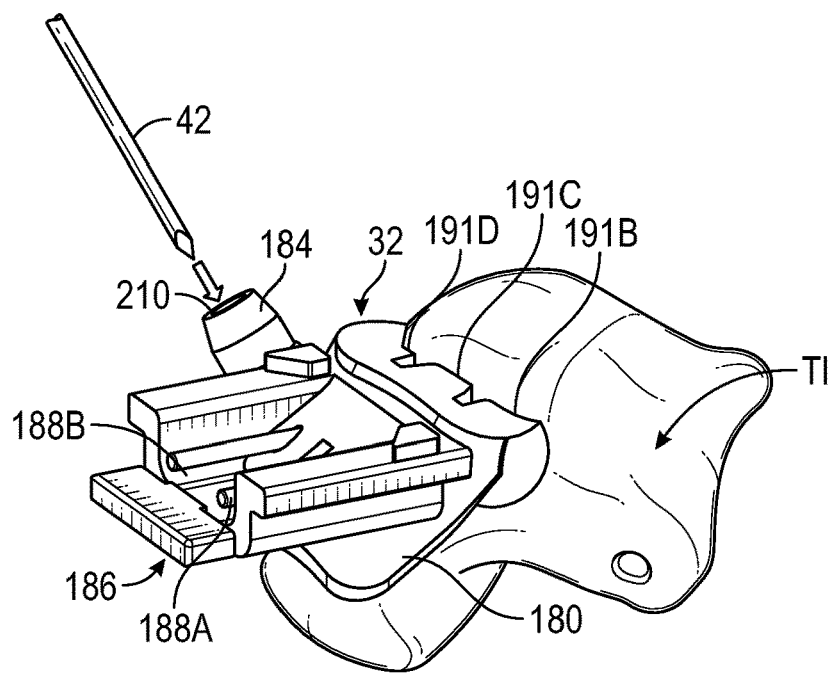
FIG. 19 is a perspective view of the patient-specific talus guide body of FIGS. 8A-8G being fastened to an anterior side of a proximal end of a talus.

FIG. 19 is a perspective view of patient-specific talus guide body 32 of FIGS. 8A-8D being fastened to an anterior side of a proximal end of talus Tl. Patient-specific surface 190 of bone-engaging body 180 can be engaged with the anterior side of talus Tl. Pads 191A-191D can be engaged with corresponding landmarks on talus Tl as are determined pre-operatively in the surgical plan. Bone-engaging body 180 can be pushed down against the talus neck until a locking position is reached via pads 191A-191D. Body 180 can be held in place against talus Tl and pin 42 can be inserted into bore 210 of anchor body 184. In examples, pin 42 can comprise a 2.4 mm×120 mm guide wire. Dowel pins 188A and 188B can be pre-installed in body 180, such as during the manufacturing of patient-specific talus guide body 32 for the receipt of talus cutting resection block 34.

Figure 20:
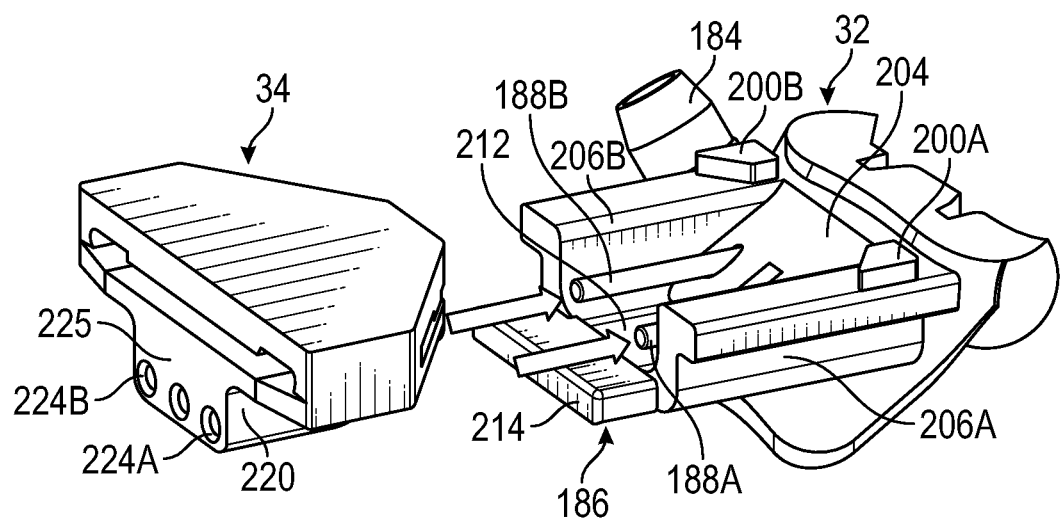
FIG. 20 is a perspective view of the talus resection block of FIGS. 9A-9D being assembled with the patient-specific talus guide body of FIG. 19.

FIG. 20 is a perspective view of talus resection block 34 of FIGS. 9A-9D being assembled with patient-specific talus guide body 32. Talus Tl and pin 42 are omitted from FIG. 20, but talus resection block 34 can be assembled to talus guide body 32 while talus guide body 32 is attached to talus Tl. Talus resection block 34 can be attached to dowel pins 188A and 188B by sliding bores 224A and 224B over pins 188A and 188B, respectively. Talus resection block 34 can be pushed into engagement with talus guide body 32 until posterior surface 226 engages posterior portion 204. Likewise, angled engagement surfaces 236A and 236B can be pushed into engagement with angled engagement surfaces 208A and 208B, respectively. As talus resection block 34 is being slid, posterior surface 226 can engage locking device 186. In particular, posterior surface 226 can engage projection 214 and push projection 214 downward to cause flexing of cantilevered body 212. As such, coupling block 220 can slide over projection 214. When talus resection block 34 is fully seated, projection 214 will extend from cantilevered body 212 against anterior surface 225 of coupling block 220, thereby locking talus resection block 34 into patient-specific talus guide body 32. Furthermore, as can be seen in FIG. 2, when talus resection block 34 is properly seated within inferior cup 196 (FIG. 8D) of patient-specific talus guide body 32, anterior surface 225 will be flush, even or co-planar with anterior faces of sloped portions 206A and 206B (FIG. 8D), thereby providing a visual indication to a surgeon that the device has been assembled properly.

FIG. 21 is a perspective view of talus stylus 290 inserted into talus resection block 34 of the assembly of FIG. 20. Talus stylus 290 can comprise u-shaped body 292, plate 294, fins 296A-296D and viewer 298. After talus resection block 34 is assembled with patient-specific talus guide body 32, pin 46 can be inserted into bore 224C and extended through channel 194 (FIG. 8C) and into talus Tl.

Plate 294 can be inserted into cutting guide slot 230 of talus resection block 34. Plate 280 can provide a wide point of contact between stylus 290 and talus resection block 34 to ensure proper alignment of u-shaped body 292 with patient-specific talus guide body 32. U-shaped body 292 can comprise transverse extension 292A and sagittal arms 292B and 292C. Transverse extension 292A can be configured to extend medial-laterally beyond talus Tl and soft tissue attached thereto to allow sagittal arms 292A and 292B to be positioned alongside talus Tl. Arms 292A-292C can be configured to be co-planar such that when stylus 290 is viewed from the side, arms 292B and 292C can be behind each other. Fins 296A-296D can extend perpendicularly from arm 292B. Stylus 290 can be fabricated from a radiopaque material such that stylus 290 can be viewed in imaging, such as x-ray imaging.

Figure 22:
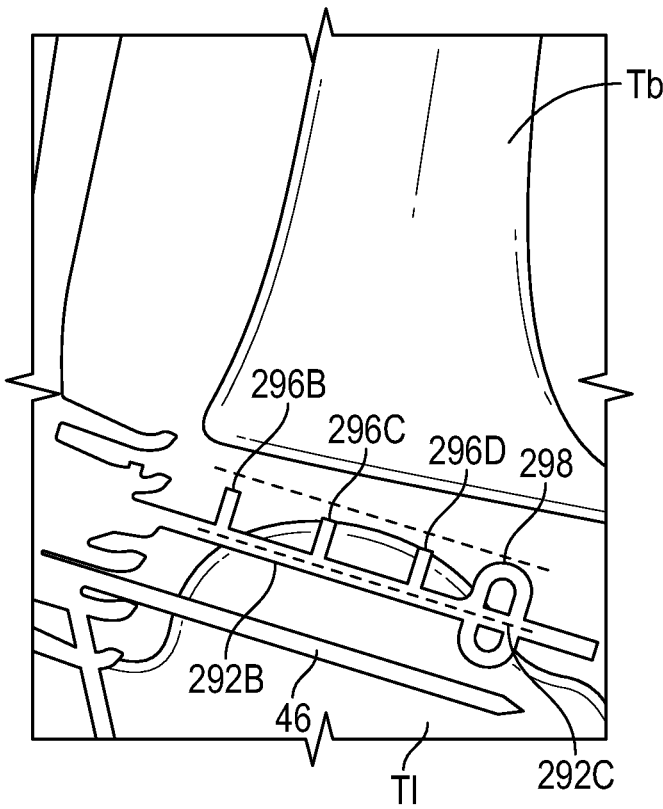
FIG. 22 is a schematic view of imaging of the talus stylus of FIG. 21 indicating a resection height for the talus.

FIG. 22 is a schematic view of imaging of talus stylus 290 of FIG. 21 indicating a resection height or depth for talus Tl. Imaging of FIG. 22 is taken from a medial-lateral side of patient-specific talus guide body 32 in a lateral plane such that arm 292C is behind arm 292B. A distal portion of arm 292C can be viewed through an opening in viewer 298, which can comprise a targeting slot. As can be seen in FIG. 22, arms 292B and 292C extend in parallel. With arms 292A and 292C extending in parallel a true view of the position of talus guide body 32 on talus Tl. Thus, the amount of bone that is configured to be removed from the proximal end of talus Tl can be viewed. In particular, the perpendicular extension of fins 296A-296D can be seen. The length of fins 296A-296D can each correspond to a desired resection thickness of talus Tl. In examples, fins 296A-296D can comprise tabs having lengths of 6.4 mm. Those of fins 296A-296D pointing to the most proximal portion of the proximal end of talus Tl indicate proper positioning of talus resection guide body 32. In an example, the length of fins 296A-296D can represent the amount of bone appropriate for removal to implant talus bearing component 66. As discussed, placement of talus cut guide 12 on talus Tl and hence placement of cutting guide slot 230 can be determined according to a pre-operative surgical plan. If fins 296A-296D indicate that too much or too little bone is to be removed per the installation of talus guide body 32, the surgical plan can be altered or resection of talus Tl can be performed using other instrumentation, such as non-patient-specific cutting guides.

Figure 23:
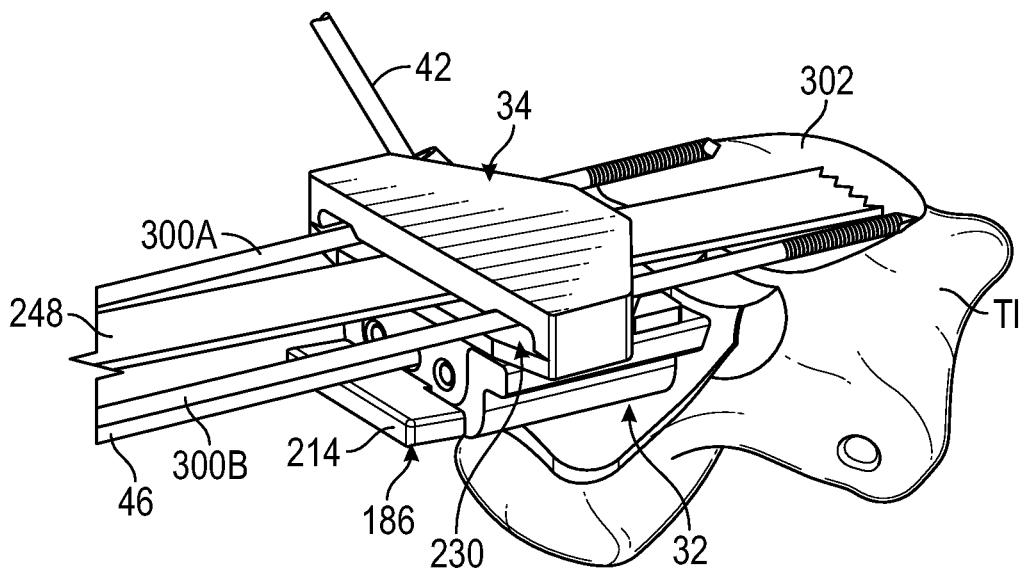
FIG. 23 is a perspective view of a resection blade inserted through a cutting guide slot of the talus resection block of the assembly of FIG. 20.

FIG. 23 is a perspective view of resection blade 298 inserted through cutting guide slot 230 of talus resection block 34 of the assembly of FIG. 20. Pins 300A and 300B can be inserted into cutting guide slot 230 and inserted into talus Tl. Pins 300A and 300B can comprise 2.4 mm threaded K-wires. In examples, pin 300A can be 120 mm in length and pin 300B can be 135 mm in length, but in other examples both of pins 300A and 300B can have the same length of 120 mm or 135 mm, depending on the patient and the specifics of the procedure to be performed. Troughs 234A and 234B can be used to facilitate insertion of pins 300A and 300B into cutting guide slot 230, respectively. After pins 300A and 300B are implanted, resection blade 298 can be inserted into slot 230 and operated to resect the proximal portion of talus Tl, such as via oscillatory or reciprocating motion. Care should be taken to avoid damage to neurovascular structures.

Figure 24:
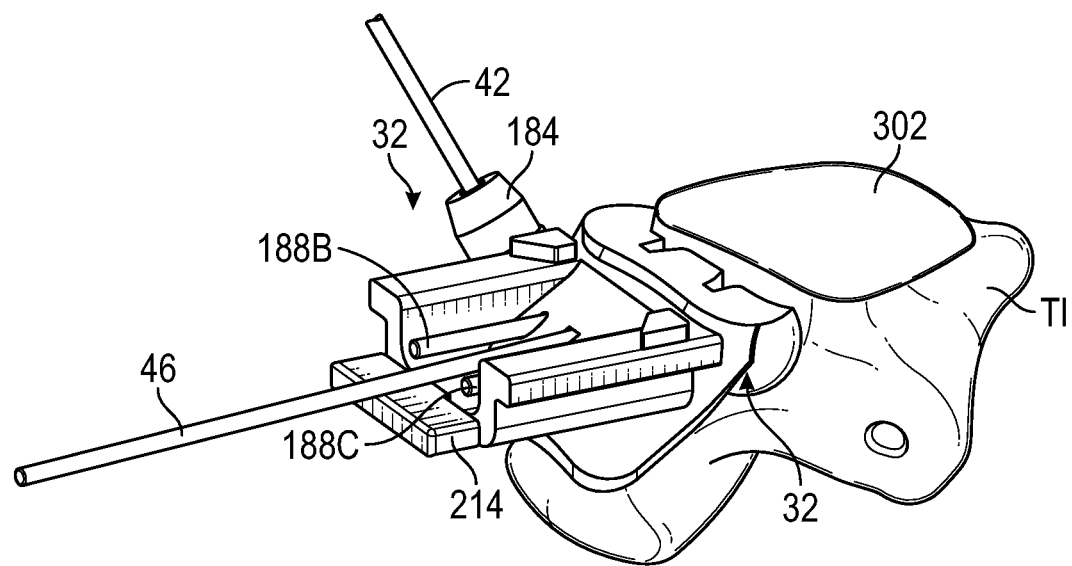
FIG. 24 is a perspective view of the talus with the proximal end resected to form a planar surface.

FIG. 24 is a perspective view of talus Tl with the proximal end being resected to form resected surface 302. Pins 300A and 300B can be removed from talus resection block 34 and talus resection block 34 can be removed from patient-specific talus guide body 32. Talus resection block 34 can be removed by depressing projection 214 to flex cantilevered body 212 and to allow talus resection block 34 to slide past projection 214. Talus guide body 32 can remain attached to talus Tl via pins 42 and 46.

Figure 25:
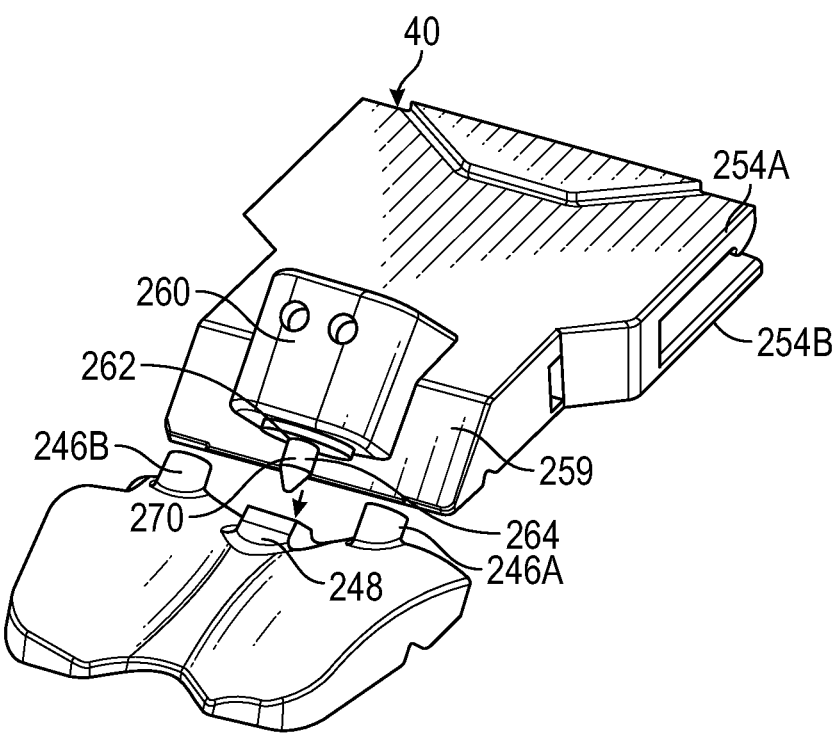
FIG. 25 is a perspective view of the floating talar trial and floating talar guide of FIGS. 10A-10E being assembled.

FIG. 25 is a perspective view of floating talar trial 38 and floating talar guide 40 of FIGS. 10A-10C being assembled. Fastener 264 can be positioned within fastener bore 262 of fastener block 260 such that the tip of threaded portion 270 protrudes therefrom. Floating talar trial 28 can then be positioned proximate floating talar guide 40 such that bore 244C of socket 248 aligns with fastener bore 262. Threaded portion 270 can then be rotated to be put in threaded engagement with bore 244C such that engagement face 259 of floating talar guide 40 contacts engagement face 251 of floating talar trial 38. In an example, a BT10 Hexalobular Torque Handle can be used to rotate head 266 of fastener 264.

The size of floating talar trail 38 can be selected based on the preoperative surgical plan. Floating talar guide 40 can be provided with indicia indicating the size of each specific floating talar guide. Floating talar guide 40 can also be provided with indicia indicating the proper orientation (e.g., which side of floating talar guide 40 is the top surface) of floating talar guide 40 relative to talus resection block 34.

Figure 26:
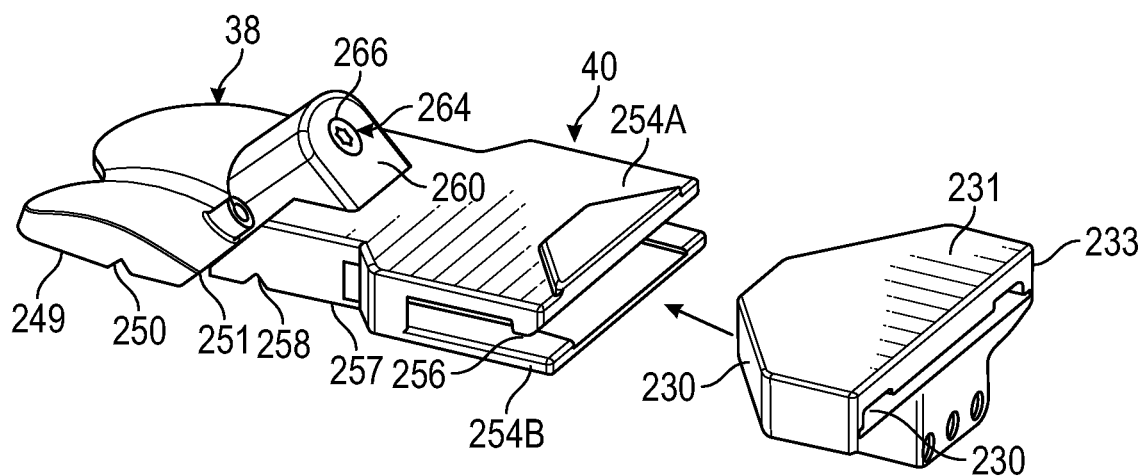
FIG. 26 is a perspective view of talus resection block of FIGS. 9A-9D being assembled with the floating talar guide of FIG. 25.

FIG. 26 is a perspective view of talus resection block 34 of FIGS. 9A-9D being assembled with floating talar guide 40 of FIG. 25. Second flange 254B of floating talar guide 40 can be inserted into cutting guide slot 230 of talus resection block 34 such that first flange 254A extends across superior surface 231 of talus resection block 34. As can be seen in FIGS. 27 and 2, lip 256 can extend inward from first flange 254A to engage anterior surface 233 of talus resection block 34. Lip 256 can thereby lock talus resection block 34 into engagement with floating talar guide 40. Lip 256 can additionally provide a surgeon with visual confirmation of the assembly of floating talar guide 40 and talus resection block 34. With talar guide 40 and talar trial 38 assembled, inferior surfaces 257 and 249 can align. As such, the floating position of talar guide 40 and talar trial 38 relative to resected surface 302 can be viewed using imaging.

Figure 27:
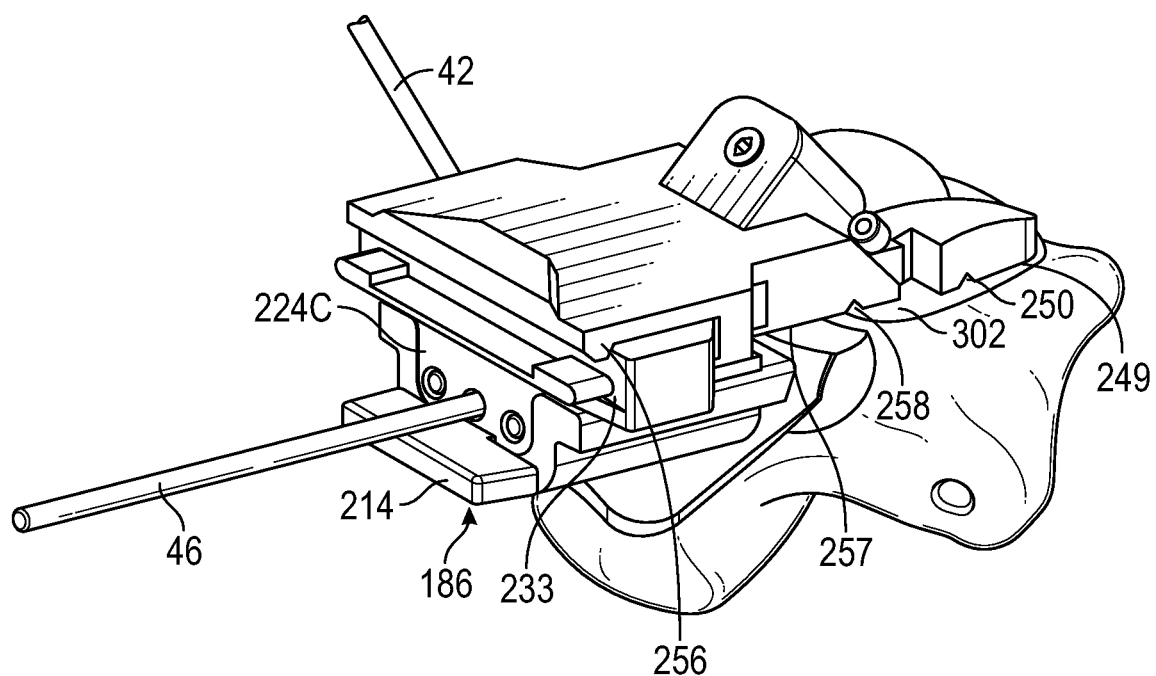
FIG. 27 is a perspective view of the talus resection block of FIG. 26 assembled with the patient-specific talus guide body of FIG. 24.

FIG. 27 is a perspective view of talus resection block 34 of FIG. 26 assembled with patient-specific talus guide body 32 of FIG. 24. Talus resection block 34, as assembled with floating talar guide 40 and floating talar trial 38, can be attached to patient-specific talus guide body 32 by inserting pin 46 into bore 224C to again seat curved sides 228A and 288B of coupling block 220 in sloped portions 206A and 206B of inferior cup 196. Projection 214 of locking device 186 can again be used to secure the placement of talus resection block 34 to talus guide body 32. Floating talar guide 40 can extend from talar resection block 34, beyond talus guide body 32, and extend over resected surface 302. Floating talar trial 38 can extend from floating talar guide 40 against resected surface 302 in position to simulate the final placement of talar bearing component 66. Anterior-posterior position and rotation of floating talar trial 40 can be planned as per the pre-operative surgical plan for the case.

Figure 28:
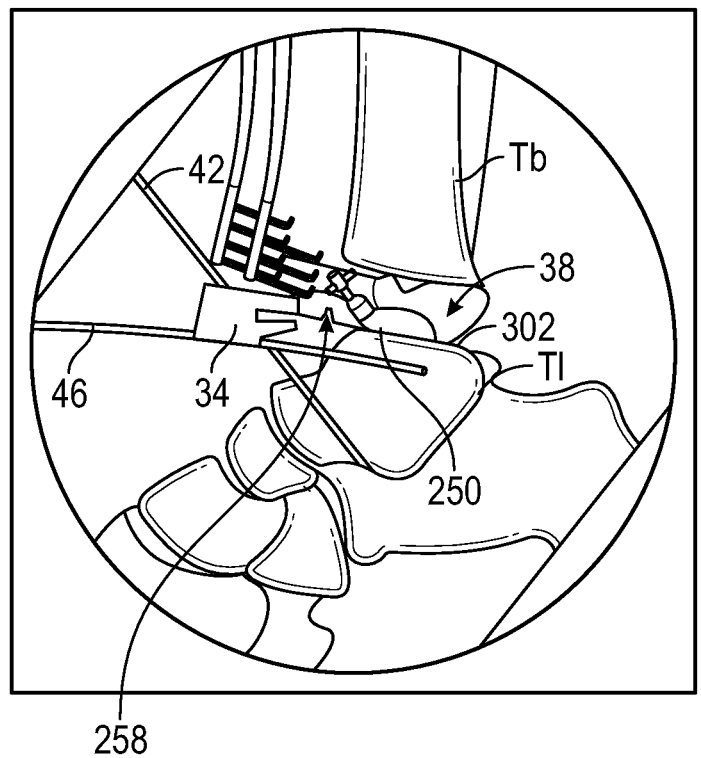
FIG. 28 is a schematic view of imaging of the floating talar trial and floating talar guide of FIG. 27 showing anterior-posterior position.

FIG. 28 is a schematic view of imaging of floating talar trial 38 of FIG. 27 showing anterior-posterior position. The imaging of FIG. 28 is taken from a medial-lateral side of floating talar trial 38 in a lateral plane such that arm 292C is behind arm 292B. Position of floating talar guide 40 and floating talar trial 38 can be verified as per the approved surgical plan using fluoroscopy. Indicator notches 250 and 258 of floating talar trial 38 and floating talar guide 40, respectively, can be used to verify the anterior-posterior position of floating talar trail 38 and floating talar guide 40 relative to resected surface 302. The locations of indicator notches 250 and 258 relative to the overall lengths of floating talar trial 38 and floating talar guide 40 can be known or predetermined in advance of the surgical procedure in order to, for example, assist in determining the position of floating talar trial 38 relative to the anatomy.

Figure 29:
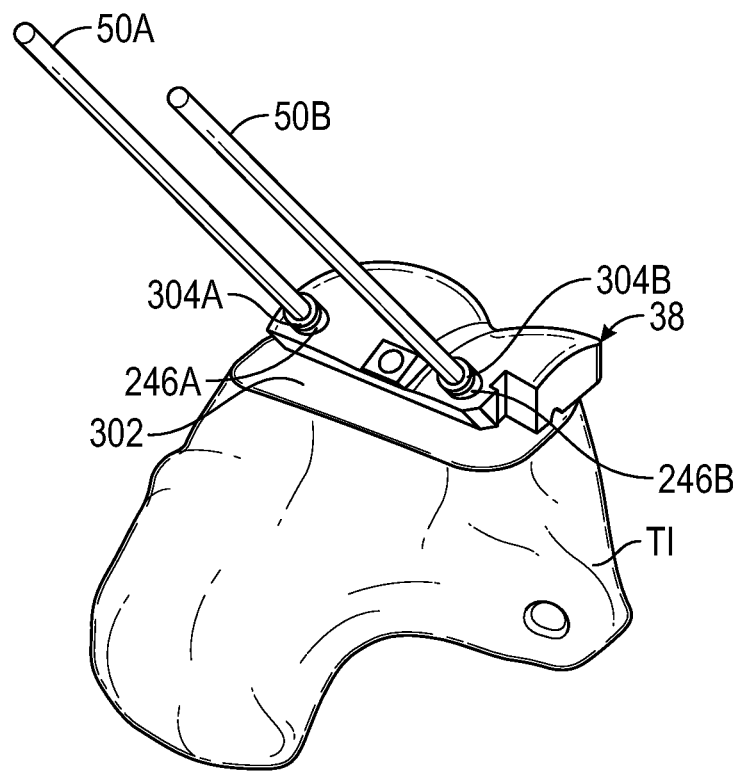
FIG. 29 is a perspective view of the floating talar trial of FIG. 28 held in place via guide pins and the floating talar guide and patient-specific talus guide body removed.

FIG. 29 is a perspective view of floating talar trial 38 of FIG. 28 held in place via guide pins 50A and 50B and floating talar guide 40 and patient-specific talus guide body 32 removed. Pins 50A and 50B can be inserted into and through bores 244A and 244B in collars 246A and 246B, respectively, to engage bone of resected surface 302. Pins 50A and 50B can be drilled into floating talar trial 38 until heads 304A and 304B are flush with collars 246A and 246B, respectively. The heel can be pushed up while inserting pins 50A and 50B to prevent floating talar trial 38 from moving. Position of floating talar trial 38 can be confirmed with fluoroscopy imaging to ensure floating talar trial 38 did not move and is placed according to the surgical plan.

Figure 30:
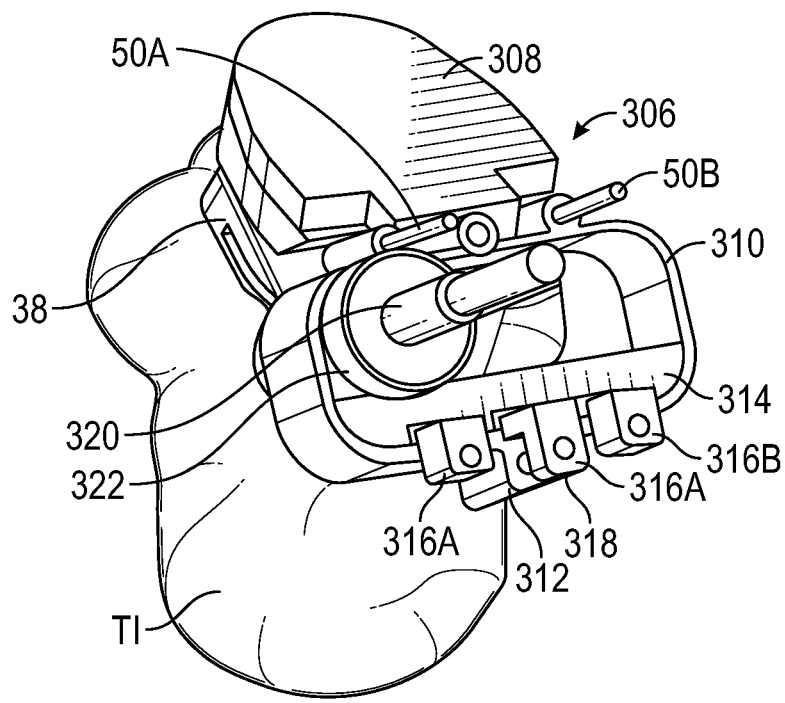
FIG. 30 is a perspective view of an anterior resection guide attached to the guide pins of FIG. 29.

FIG. 30 is a perspective view of anterior resection guide 306 attached to guide pins 50A and 50B of FIG. 29. Anterior resection guide 306 can be sized appropriately for the specific patient based on bone size, according to the preoperative surgical plan. Anterior resection guide 206 can comprise chamfer guide body 308 and reamer guide 310. Chamfer guide body 308 can be positioned against floating talar trial 38 and locked thereto with a fastener, such as a BT10 Hexalobular Torque set screw. A center boss of anterior resection guide 306 can be positioned flush with a center boss on floating talar trial 38. Pin 318, such as a long 2.4 mm guide wire, can be placed through distal bore 312 in reamer guide 310 for additional fixation.

Spacer 314 can be positioned within reamer guide 310 in two positions for reaming the distal and inferior portions of talus Tl. Flange 316A can be attached to pin 318 inserted into bore 312 for reaming the inferior portion of talus Tl. Flanges 316B and 316C can be attached to pins 50A and 50B, respectively, for reaming the distal portion of talus Tl. With spacer 314 in either position, reamer 320 can be ran back and forth within reamer guide 310 until hard stop 322 rests on reamer guide 310.

Figure 31:
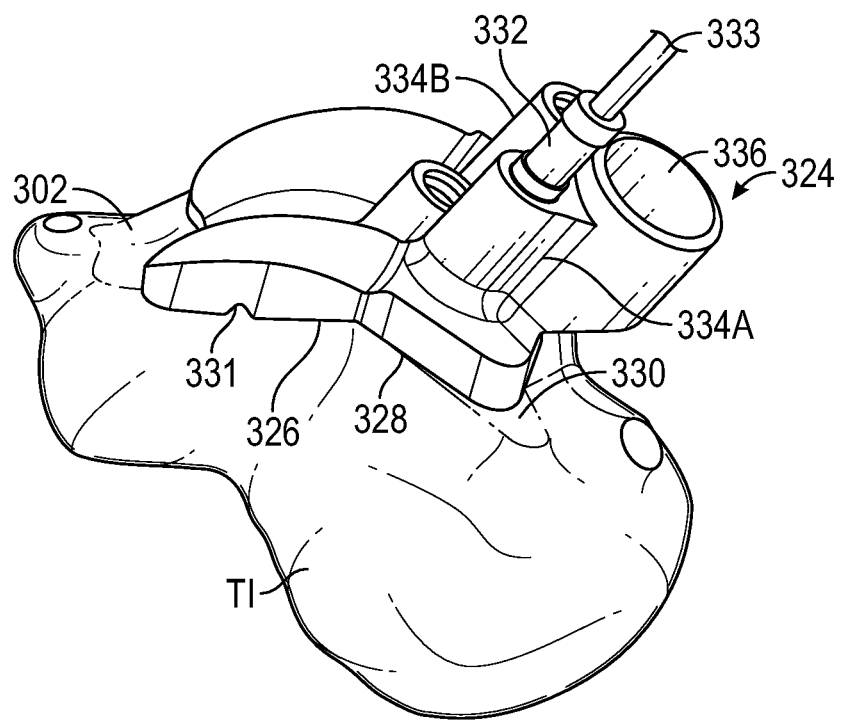
FIG. 31 is a perspective view of a talar sulcus guide attached to the talus bone after anterior resecting of FIG. 30.

FIG. 31 is a perspective view of talar sulcus guide 324 attached to talus Tl after anterior resecting of FIG. 30. Surfaces 326 and 328 of talar sulcus guide 324 can be mated flush with resected surface 302 and resected surface 330. Resected surface 330 can be formed according to the procedure performed with respect to FIG. 30. Medial-lateral position of talar sulcus guide 324 can be confirmed according to the surgical plan to ensure proper medial-lateral positioning of talar bearing component 66. Fluoroscopy can be used to evaluate the position of talar sulcus guide 324 and notch 331 can be used to verify that a true sagittal image is achieved.

Peg 332 can be inserted into one of sockets 334A and 334B of talar sulcus guide. Peg 332 can include a bore for receiving guide wire 333 to hold talar sulcus guide 324 in place. The other of sockets 334A and 334B into which peg 332 is not inserted can then be used to ream a first peg hole for talar bearing component 66. The position of peg 332 and the reamer can then be switched to ream a second peg hole for talar bearing component 66. The reamer can include a hard stop to engage sockets 334A and 334B when reaming is sufficiently deep.

Figure 32:
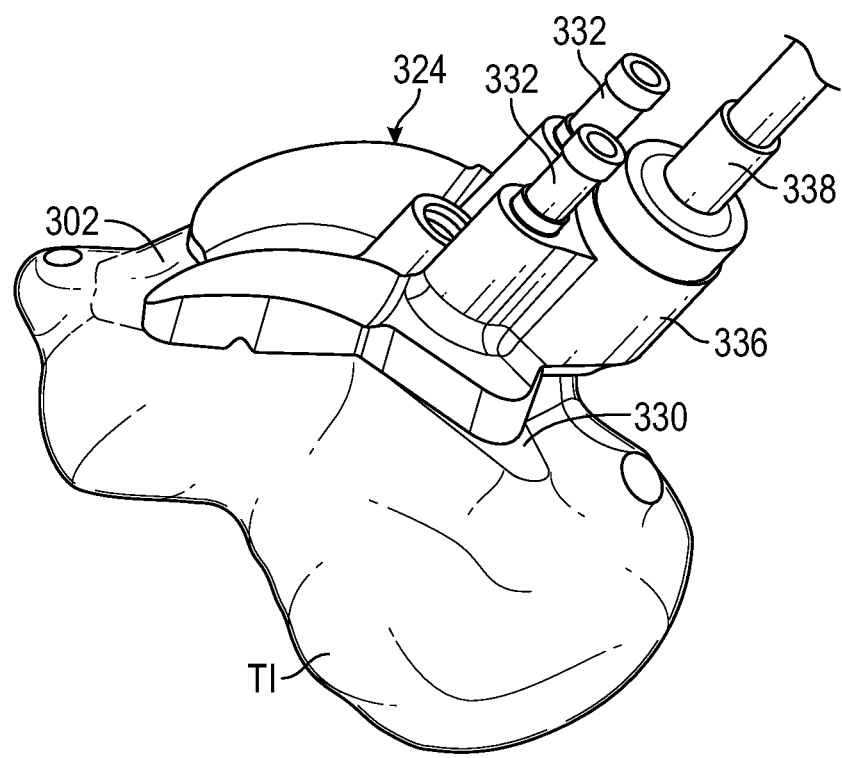
FIG. 32 is a perspective view of the talar sulcus guide of FIG. 31 being held in place with pegs and a reaming device inserted therein.

FIG. 32 is a perspective view of talar sulcus guide 324 of FIG. 31 being held in place with a pair of pegs 332. Socket 336 can be used to ream the sulcus of talus Tl to facilitate reception of talar bearing component 66. Reaming device 338 can be inserted into socket 336 to remove bone. A hard stop can be provided on reaming device 338 to engage socket 336 when reaming is sufficiently deep.

Figure 33:
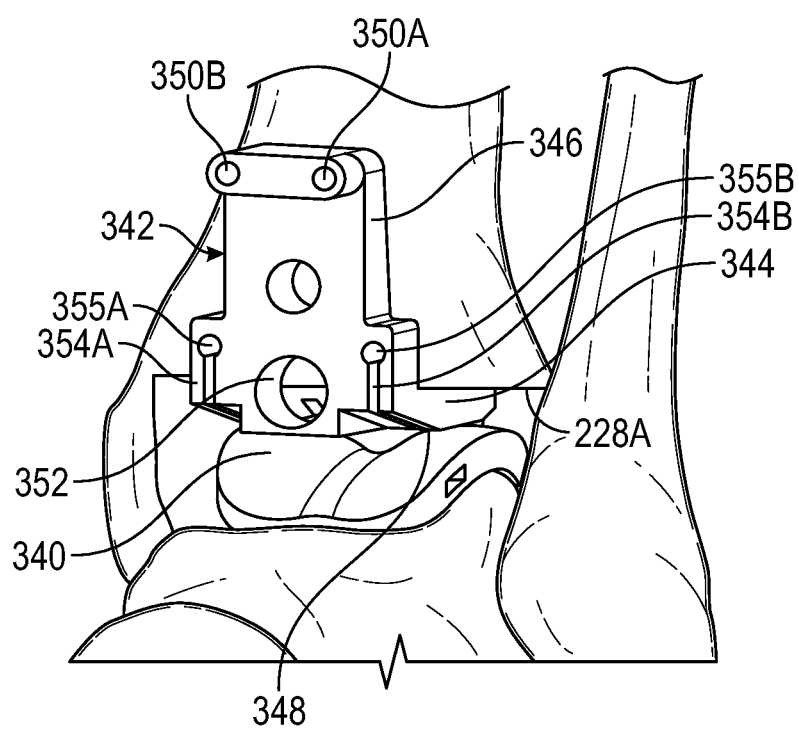
FIG. 33 is a perspective view the ankle joint formed by the tibia and talus with a talar bearing component attached to the talus and a floating tibial trial positioned against the tibia.

FIG. 33 is a perspective view the ankle joint formed by tibia Tb and talus Tl with talar bearing component 340 attached to talus Tl and floating tibial trial 342 positioned against tibia Tb. Pegs of talar bearing component 340 can inserted into the peg holes reamed with reference to FIG. 31. Talar bearing component 340 can comprise a trial used to simulate talar bearing component 66 and to facilitate placement of floating tibial trail 342 to, for example, set the tension in the ankle joint. Distal surface 344 of floating tibial trial 342 can be placed against resected surface 228A and posterior surface 346 can be placed against anterior surface of tibia Tb. Bearing surface 348 can engage talar bearing component 340. Pins can be inserted into bores 350A and 350B to hold floating tibial trial 342 in place. A drill can be inserted into socket 352 to prepare tibia Tb for receiving protrusion 72 of talar bearing component 66. A saw can be inserted into slots 354A and 354B to prepare tibia Tb for receiving fixation devices 70A and 70B of talar bearing component 66. A drill can be inserted into bulbous end portions 355A and 355B of slots 354A and 354B to form guide pin holes 359A and 359B in tibia Tb that can be used to implant tibial bearing component 62 and tibial tray component 64.

Figure 34:
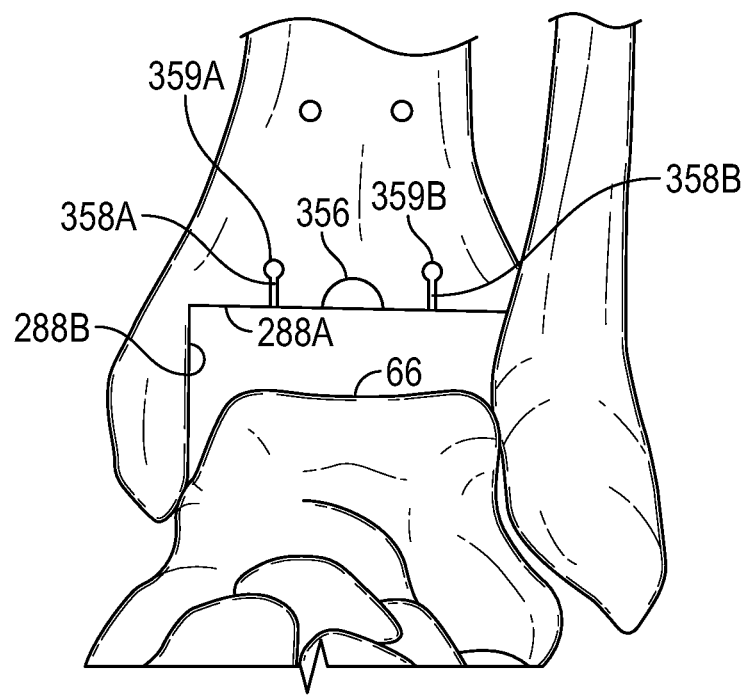
FIG. 34 is a perspective view of the ankle joint of FIG. 33 showing the tibia as resected via the floating tibial trial.

FIG. 34 is a perspective view of the ankle joint of FIG. 33 showing tibia Tb as resected via floating tibial trial 342. Receptacle 356 can be formed in tibia Tb into which protrusion 72 can abut. Slots 358A and 358B can be formed in tibia Tb into which fixation devices 70A and 70B can be inserted. Pin bores 359A and 359B can be formed in tibia Tb into which pins 362A and 362B (FIG. 35) can be inserted to facilitate insertion of tibial bearing component 62 and tibial tray component 64.

Figure 35:
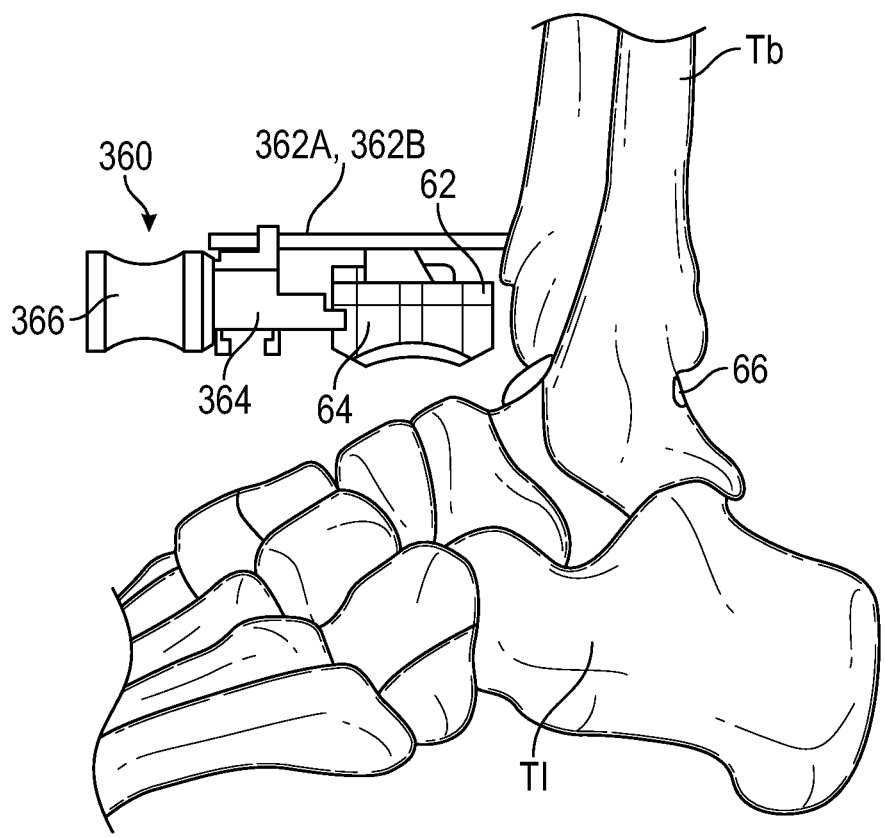
FIG. 35 is a side view of the ankle joint of FIG. 34 showing an insertion tool being used to implant an assembled tibial tray component and tibial bearing component into the tibia.

FIG. 35 is a side view of the ankle joint of FIG. 34 showing insertion tool 360 being used to implant an assembled tibial tray component 64 and tibial bearing component 62 into tibia Tb. Pins 362A and 362B can be inserted into pin bores 359A and 359B. Base 364 of insertion tool 360 can include an attachment feature for attaching to a mating feature on one or both of tibial bearing component 62 and tibial tray component 64. Base 364 can additionally include holes for receiving pins 362A and 362B to facilitate sliding of insertion tool 360 straight (e.g., in an anterior-posterior direction) into tibia Tb. In particular, fixation devices 70A and 70B can be slid straight into slots 358A and 358B, and protrusion 72 can be slid straight into receptacle 356. Handle 366 can be attached to base and can be used to receive an impact from an impactor, such as a hammer. Talus bearing component 66 and tibial tray component 64 can be secured in place using bone cement.

VARIOUS NOTES & EXAMPLES

Example 1 can include or use subject matter such as a patient-specific guide system for performing a talus resection for a total ankle arthroplasty that can comprise a talus guide body that can comprise a first patient-specific surface for engaging at least a portion of an anterior surface of a talus, a first pin hole extending through the talus guide body, and a first socket extending into the talus guide body; a talus resection block that can comprise a coupling block removably insertable into the first socket, a second pin hole configured to align with the first pin hole, and a guide block including a resection guide surface; a floating talar guide couplable to the talus resection block and configured to extend beyond the first patient-specific surface; and a floating talar trial couplable to the floating talar guide, the floating talar trial including a bearing surface and being configured to extend co-planar with the resection guide surface.

Example 2 can include, or can optionally be combined with the subject matter of Example 1, to optionally include a talus guide body that is fabricated from a plastic material and the talus resection block is fabricated from a metal material.

Example 3 can include, or can optionally be combined with the subject matter of one or any combination of Examples 1 or 2 to optionally include a metal bushing in the first pin hole.

Example 4 can include, or can optionally be combined with the subject matter of one or any combination of Examples 1 through 3 to optionally include a floating talar guide that is couplable to the talus resection block via interface with the resection guide surface.

Example 5 can include, or can optionally be combined with the subject matter of one or any combination of Examples 1 through 4 to optionally include an interface body for attaching to the floating talar trial, a first flange extending from the interface body for extending along the resection guide surface, and a second flange extending from the interface body in opposing relationship to the first flange for clipping over the talus resection block.

Example 6 can include, or can optionally be combined with the subject matter of one or any combination of Examples 1 through 5 to optionally include a second flange that includes a lip for engaging an anterior face of the talus resection block.

Example 7 can include, or can optionally be combined with the subject matter of one or any combination of Examples 1 through 6 to optionally include a floating talar trial that can comprise a trail body comprising an interface for engaging the floating talar guide, and a bearing surface located at a superior side of the trial body Example 8 can include, or can optionally be combined with the subject matter of one or any combination of Examples 1 through 7 to optionally include an interface that can comprise a threaded fastener.

Example 9 can include, or can optionally be combined with the subject matter of one or any combination of Examples 1 through 8 to optionally include a pair of guide bores extending into the trial body at an angle relative to an inferior surface of the floating talar guide at which the threaded fastener extends.

Example 10 can include, or can optionally be combined with the subject matter of one or any combination of Example 1 through 9, to optionally include a floating talar guide that can include a first inferior surface and the floating talar trial includes a second inferior surface, and a first inferior surface and a second inferior surface that can be configured to align when engaged at the interface.

Example 11 can include, or can optionally be combined with the subject matter of one or any combination of Example 1 through 10, to optionally include a first indentation on the first inferior surface visible from a medial or lateral side of the floating talar guide, a second indentation on the second inferior surface visible from a medial or lateral side of the floating talar trial.

Example 12 can include, or can optionally be combined with the subject matter of one or any combination of Example 1 through 11, to optionally include a spring-actuated locking device to prevent the talus resection block from backing out of the first socket when the talus resection block is fully seated in the first socket.

Example 13 can include, or can optionally be combined with the subject matter of one or any combination of Examples 1 through 12 to optionally include a talus guide body that can further comprise a bottom wall extending out of the talus guide body in a direction opposite the patient-specific surface, and first and second sidewalls extending from the bottom wall to define the socket above the bottom wall.

Example 14 can include, or can optionally be combined with the subject matter of one or any combination of Examples 1 through 13 to optionally include a spring-actuated locking device that can comprise a cantilevered projection extending forward of the first and second walls above the bottom wall.

Example 15 can include, or can optionally be combined with the subject matter of one or any combination of Examples 1 through 14 to optionally include an anterior face of the talus resection block that can be flush with forward faces of the first and second sidewalls when the talus resection block is fully seated in the first socket.

Example 16 can include, or can optionally be combined with the subject matter of one or any combination of Examples 1 through 15 to optionally include a first pin hole that can be within the first socket.

Example 17 can include, or can optionally be combined with the subject matter of one or any combination of Examples 1 through 16 to optionally include a third pin hole within the socket, wherein the first pin hole and the third pin hole lie in a plane parallel to the resection guide surface.

Example 18 can include, or can optionally be combined with the subject matter of one or any combination of Examples 1 through 17 to optionally include a talar resection block that can further comprise a resection slot in the guide block that is partially defined by the resection guide surface.

Example 19 can include, or can optionally be combined with the subject matter of one or any combination of Examples 1 through 18 to optionally include a guide block that can include a pair of angled surfaces that define an angle bisected by a center of the cut guide body, and a talus guide body that can further comprise a pair of angled stops configured to flushly engage the pair of angled surfaces, respectively.

Example 20 can include, or can optionally be combined with the subject matter of one or any combination of Examples 1 through 19 to optionally include a medial-lateral anchor bushing that can extend from the talus guide body oblique to the first pin hole.

Example 21 can include or use subject matter such as a method for performing a total-ankle arthroplasty that can comprise resecting a portion of a tibia bone, attaching a patient-specific talus guide body to a superior portion of a talus bone, attaching a size-specific talus cutting block to the patient-specific talus guide body, resecting a superior portion of the talus, attaching a talus trialing component to the talus cutting block, confirming position of the talus trialing component, coupling the talus trialing component to the talus bone, removing the talus cutting block and the patient-specific talus guide body from the talus bone, chamfering an anterior portion of the talus bone using a chamfer guide attached to the talus trialing component, and attaching prosthetic ankle components to the resected tibia and talus bones.

Example 22 can include, or can optionally be combined with the subject matter of Example 21, to optionally include resecting the portion of the tibia by: attaching a size-specific tibial cutting block to a patient-specific tibia guide body, and attaching the patient-specific tibia guide body to an inferior portion of the tibia.

Example 23 can include, or can optionally be combined with the subject matter of one or any combination of Examples 21 or 22 to optionally include confirming alignment of the tibial cutting block using a cut-depth-indicating stylus inserted into a cutting guide slot of the size-specific tibial cutting block.

Example 24 can include, or can optionally be combined with the subject matter of one or any combination of Examples 21 through 23 to optionally include attaching the talus trialing component to the talus cutting block by: removing the talus cutting block from the patient-specific talus guide body, and attaching the talus trialing component to the talus cutting block at a cutting guide surface.

Example 25 can include, or can optionally be combined with the subject matter of one or any combination of Examples 21 through 24 to optionally include attaching the talus trialing component to the talus cutting block by: attaching a floating talar trial to a floating talar guide, and attaching the floating talar guide to the talus cutting block.

Example 26 can include, or can optionally be combined with the subject matter of one or any combination of Examples 21 through 25 to optionally include attaching a floating tibial trial to the tibia as resected, and cutting tibial tray attachment slots into the tibia.

Example 27 can include, or can optionally be combined with the subject matter of one or any combination of Examples 21 through 26 to optionally include confirming position of the talus trialing component by viewing anterior-posterior position of an indicator feature on the talus trialing component relative to the resected superior surface of the talus.

Example 28 can include, or can optionally be combined with the subject matter of one or any combination of Examples 21 through 27 to optionally include chamfering an anterior portion of the talus using a chamfer guide attached to the talus trialing component by: attaching a talar chamfer guide body to pins holding the talus trialing component to the talus to position the talar chamfer guide body against the talus trialing component and position a reamer guide proximate the anterior portion of the talus, and reaming the anterior portion of the talus by moving a reamer within the reamer guide.

Example 29 can include, or can optionally be combined with the subject matter of one or any combination of Examples 21 through 28 to optionally include confirming alignment of the talus cutting block using a cut-depth-indicating stylus inserted into a cutting guide slot of the size-specific talus cutting block.

Example 30 can include or use subject matter such as a patient-specific guide for performing a bone resection for a total ankle arthroplasty that can comprise: a bone guide body that can comprise: a patient-specific surface for engaging a surface of a talus or a tibia, a first pin hole extending through the bone guide body, and a first socket extending through the bone guide body, and a bone resection block removably insertable into the first socket and configured to receive a first pin that can be inserted in the first pin hole, the bone resection block including a resection guide surface.

Example 31 can include, or can optionally be combined with the subject matter of Example 30, to optionally include a forward surface of the first socket that can be configured to align co-planarly with a forward face of the bone resection block when the bone resection block is fully seated in the first socket.

Example 32 can include, or can optionally be combined with the subject matter of one or any combination of Examples 30 or 31 to optionally include a first pin hole that can extend along an axis that is parallel with the resection guide surface when the bone resection block is fully seated in the first socket.

Example 33 can include, or can optionally be combined with the subject matter of one or any combination of Examples 30 through 32 to optionally include a pin body coupled to the bone guide body configured to receive an anchor pin.

Example 34 can include, or can optionally be combined with the subject matter of one or any combination of Examples 30 through 33 to optionally include a pin body that can comprise a pin block including a plurality of through-bores for receiving pins parallel to the first pin hole.

Example 35 can include, or can optionally be combined with the subject matter of one or any combination of Examples 30 through 34 to optionally include a pin body that can comprise a cylindrical projection extending from the bone guide body including a through-bore for receiving a pin oblique to the first pin hole.

Example 36 can include, or can optionally be combined with the subject matter of one or any combination of Examples 30 through 35 to optionally include alignment features to facilitate alignment of the bone resection block with the first socket.

Example 37 can include, or can optionally be combined with the subject matter of one or any combination of Examples 30 through 36 to optionally include a alignment features that can comprise a pair of biasing elements located within the first socket to push the bone resection block against wall surfaces of the first socket.

Example 38 can include, or can optionally be combined with the subject matter of one or any combination of Examples 30 through 37 to optionally include alignment features that can comprise a pair of angled stops configured to engage angle walls of the bone resection block.

Example 39 can include, or can optionally be combined with the subject matter of one or any combination of Examples 30 through 38 to optionally include a snap-lock feature to receive an alignment pin orthogonal to the first pin hole.

Example 40 can include, or can optionally be combined with the subject matter of one or any combination of Examples 30 through 39 to optionally include a locking device to hold the bone resection block in the first socket.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

The claimed invention is:

1. A patient-specific guide system for performing a talus resection for a total ankle arthroplasty, the patient-specific guide system comprising:
   a talus guide body comprising:
      a first patient-specific surface for engaging at least a portion of an anterior surface of a talus; and
      a first pin hole extending through the talus guide body;
   a talus resection block comprising:
      a coupling block;
      a second pin hole configured to align with the first pin hole; and
      a guide block including a resection guide surface; and
   a floating talar trial, the floating talar trial including a bearing surface and being configured to extend co-planar with the resection guide surface.

2. The patient-specific guide system of claim 1, wherein the talus guide body is fabricated from a plastic material and the talus resection block is fabricated from a metal material.

3. The patient-specific guide system of claim 1, further comprising a floating talar guide, wherein the floating talar guide comprises:
   an interface body for attaching to the floating talar trial.

4. The patient-specific guide system of claim 3, wherein the floating talar guide further comprises:
   a first flange extending from the interface body for extending along the resection guide surface; and
   a second flange extending from the interface body in opposing relationship to the first flange for clipping over the talus resection block;
   wherein the second flange includes a lip for engaging an anterior face of the talus resection block.

5. The patient-specific guide system of claim 3, wherein the floating talar trial includes an interface for engaging the floating talar guide;
   wherein:
   the floating talar guide includes a first inferior surface and the floating talar trial includes a second inferior surface; and
   the first inferior surface and the second inferior surface are configured to align when engaged at the interface.

6. The patient-specific guide system of claim 1, wherein the floating talar trial comprises:
   a trial body; and
   a bearing surface located at a superior side of the trial body.

7. The patient-specific guide system of claim 6, wherein the floating talar trial can be held in place by pins placed through a pair of guide bores.

8. The patient-specific guide system of claim 1, further comprising:
   a first indentation on a first inferior surface of the floating talar trial visible from a medial or lateral side of the floating talar trial.

9. The patient-specific guide system of claim 1, wherein the talus guide body further comprises:

a bottom wall extending out of the talus guide body in a direction opposite the first patient-specific surface; and first and second sidewalls extending from the bottom wall to define a first socket above the bottom wall.

10. The patient-specific guide system of claim 9, further comprising a spring-actuated locking device to prevent the talus resection block from backing out of the first socket when the talus resection block is fully seated in the first socket, wherein the spring-actuated locking device comprises a cantilevered projection extending forward of the first and second sidewalls above the bottom wall.

11. The patient-specific guide system of claim 9, further comprising:
a third pin hole within the first socket, wherein the first pin hole and the third pin hole lie in a plane parallel to the resection guide surface within the first socket; and
a medial-lateral anchor bushing extending from the talus guide body oblique to the first pin hole.

12. The patient-specific guide system of claim 9, wherein:
the guide block includes a pair of angled surfaces that define an angle bisected by a center of the talus resection block; and
the talus guide body further comprises a pair of angled stops configured to flushly engage the pair of angled surfaces, respectively;
wherein an anterior face of the talus resection block is flush with forward faces of the first and second sidewalls when the talus resection block is fully seated in the first socket.

13. A talar trial comprising:
a superior surface comprising a condylar surface;
an inferior surface opposite the superior surface, the inferior surface comprising a planar surface;
a means for affixing the talar trial to bone via a pin;
a medial sidewall connecting the superior surface and the inferior surface;
a lateral sidewall connecting the superior surface and the inferior surface opposite the medial sidewall; and
an indicator located on the medial sidewall or the lateral sidewall to provide an indication of a position of the talar trial on a resected talar surface;
wherein the means for affixing the talar trial to bone comprise pin holes extending through a body attached to the talar trial.

14. The talar trial of claim 13, wherein the means for affixing the talar trial to bone further comprises pin holes extending through the superior surface and the inferior surface.

15. The talar trial of claim 13, wherein the body comprises a floating talar guide attached to the talar trial.

16. The talar trial of claim 13, wherein the indicator comprises a notch extending through the talar trial from the medial sidewall to the lateral sidewall.

17. A talar trial apparatus comprising:
a talar trial comprising:
a superior surface comprising a condylar surface;
an inferior surface opposite the superior surface, the inferior surface comprising a planar surface;
an anterior side connecting the superior surface and the inferior surface; and
a first coupler component located at the anterior side; and
a talar extension attachable to the talar trial, the talar extension comprising:
an extension body coupled to the talar trial to facilitate insertion into an ankle joint; and
a second coupler component located on the extension body, the second coupler component configured for connecting to the first coupler component;
wherein the first coupler component comprises a bore and the second coupler component comprises a fastener insertable into the bore.

18. The talar trial apparatus of claim 17, wherein the extension body comprises a floating talar guide.

19. The talar trial apparatus of claim 17, wherein the first coupler component and the second coupler component comprise a threaded bore and a threaded fastener.

20. The talar trial apparatus of claim 17, wherein the extension body comprises a talar resection block.

* * * * *